(12) United States Patent
D'Souza et al.

(10) Patent No.: US 7,105,158 B1
(45) Date of Patent: Sep. 12, 2006

(54) METHODS OF ADMINISTERING MICROENCAPSULATED MATERIALS FOR IMMUNE MODULATED DISEASES

(75) Inventors: Martin J. D'Souza, Sugar Hill, GA (US); William Carl Oettinger, Atlanta, GA (US); James Cameron Oliver, Raleigh, NC (US)

(73) Assignee: The Corporation of Mercer University, Macon, GA (US)

( * ) Notice: Subject to any disclaimer, the term of this patent is extended or adjusted under 35 U.S.C. 154(b) by 336 days.

(21) Appl. No.: 08/740,755

(22) Filed: Nov. 1, 1996

Related U.S. Application Data

(60) Division of application No. 08/434,542, filed on May 4, 1995, which is a continuation-in-part of application No. 07/977,057, filed on Nov. 16, 1992, now abandoned.

(51) Int. Cl.
*A61K 9/50* (2006.01)
*A61K 38/16* (2006.01)
*A61K 39/395* (2006.01)

(52) U.S. Cl. ............... 424/130.1; 424/145.1; 424/158.1; 424/491; 424/499; 514/2

(58) Field of Classification Search ............ 424/130.1, 424/145.1, 172.1, 451, 455, 460, 491, 499
See application file for complete search history.

(56) References Cited

U.S. PATENT DOCUMENTS

| | | | | | |
|---|---|---|---|---|---|
| 4,818,542 | A | * | 4/1989 | DeLuca et al. | 424/491 |
| 4,962,091 | A | * | 10/1990 | Eppstein et al. | 514/2 |
| 5,690,954 | A | * | 11/1997 | Illum | 424/434 |
| 5,919,452 | A | * | 7/1999 | Le et al. | 424/133.1 |

OTHER PUBLICATIONS

S.S. Davis et al, Journ. of Controlled Release, 4, 293–302, 1987.*
J. H. Ratcliffe et al, Journ. Pharm. Pharmacol., 36, 431–436, 1984.*

* cited by examiner

*Primary Examiner*—David Saunders
(74) *Attorney, Agent, or Firm*—Jason A. Bernstein; Powell Goldstein LLP

(57) ABSTRACT

Compositions useful in treating immune modulated disease comprising an anticytokine antibody or immune active drug capable of modifying cytokine activity or modulating the immune system microencapsulated with a biodegradable nonantigenic material, such as albumin or PLGA. When the composition is introduced into a subject, it is phagocytosed by the target organ, the target organ digests the microsphere, releasing the drug or an active form or fragment thereof intracellularly. The drug then modifies the target organ function, thereby modulating it's activity. A method is disclosed for preparation of the microencapsulated composition.

15 Claims, 48 Drawing Sheets

| Time (Hours) | Cumulative % CsA Released | | |
|---|---|---|---|
| 1 | 0.00029 | ± | 0.00002 |
| 2 | 0.00029 | ± | 0.00005 |
| 4 | 0.00039 | ± | 0.00003 |
| 8 | 0.00037 | ± | 0.00002 |
| 24 | 0.00123 | ± | 0.00003 |
| 48 | 0.00216 | ± | 0.00005 |

FIG. 3

| GROUPS | STUDY DESCRIPTION | | |
|---|---|---|---|
| | 0 Hours | 1 Hour | 24 Hours |
| 1 | - | Lymphocytes 1 x 10^5 | Tritiated Thymidine (2 µCi) |
| 2 | CsA solution | Lymphocytes 1 x 10^5 | Tritiated Thymidine (2 µCi) |
| 3 | Blank microspheres + Macrophages (1 x 10^5) | Lymphocytes 1 x 10^5 | Tritiated Thymidine (2 µCi) |
| 4 | CsA microspheres + Macrophages (1 x 10^5) | Lymphocytes 1 x 10^5 | Tritiated Thymidine (2 µCi) |

FIG. 5

| Hours | 0 | 24 | 48 | 72 | 96 | 120 |
|---|---|---|---|---|---|---|
| Bacteria Only | 100 | 0 | 0 | 0 | 0 | 0 § |
| Bact + AB | 100 | 70 | 30 | 20 | 20 | 20 § |
| Bact + NA soln | 100 | 0 | 0 | 0 | 0 | 0 § |
| Bact + NA soln + AB | 100 | 10 | 10 | 10 | 10 | 10 § |
| Bact + MC-NA | 100 | 90 | 80 | 80 | 70 | 70 |
| Bact + MC-NA + AB | 100 | 100 | 100 | 100 | 100 | 100 |

FIG. 20

| Hours | 0 | 24 | 48 | 72 | 96 | 120 |
|---|---|---|---|---|---|---|
| Bacteria Only | 100 | 40 | 0 | 0 | 0 | 0 § |
| Bact + AB | 100 | 10 | 10 | 10 | 10 | 10 § |
| Bact + NA soln | 100 | 20 | 20 | 20 | 20 | 20 § |
| Bact + NA soln + AB | 100 | 20 | 20 | 20 | 20 | 20 § |
| Bact + MCNA | 100 | 100 | 100 | 100 | 40 | 40 § |
| Bact + MCNA + AB | 100 | 100 | 100 | 100 | 100 | 100 |

FIG. 21

| Hours | 0 | 24 | 48 | 72 | 96 | 120 |
|---|---|---|---|---|---|---|
| Bacteria Only | 100 | 0 | 0 | 0 | 0 | 0 § |
| Bact + AB | 100 | 70 | 30 | 20 | 20 | 20 § |
| Bact + NA soln | 100 | 10 | 10 | 10 | 10 | 10 § |
| Bact + NA soln + AB | 100 | 10 | 10 | 10 | 0 | 0 § |
| Bact + MC-NA | 100 | 90 | 60 | 50 | 20 | 20 § |
| Bact + MC-NA + AB | 100 | 100 | 100 | 100 | 100 | 100 |

FIG. 22

| Hours | 0 | 24 | 48 | 72 | 96 | 120 |
|---|---|---|---|---|---|---|
| Bacteria Only | 100 | 40 | 0 | 0 | 0 | 0 § |
| Bact + AB | 100 | 10 | 10 | 10 | 10 | 10 § |
| Bact + NA soln | 100 | 20 | 20 | 20 | 20 | 20 § |
| Bact + NA soln + AB | 100 | 0 | 0 | 0 | 0 | 0 § |
| Bact + MCNA | 100 | 70 | 50 | 50 | 0 | 0 § |
| Bact + MCNA + AB | 100 | 100 | 100 | 100 | 100 | 100 |

FIG. 23

| Sample N = 6 | 1 : 1 | 2 : 1 | 4 : 1 | 8 : 1 | 12 : 1 |
|---|---|---|---|---|---|
| 1 | 9 | 22 | 28 | 62 | 45 |
| 2 | 6 | 14 | 36 | 47 | 49 |
| 3 | 3 | 19 | 32 | 58 | 72 |
| 4 | 8 | 26 | 24 | 64 | 61 |
| 5 | 4 | 17 | 44 | 51 | 53 |
| 6 | 6 | 23 | 41 | 49 | 46 |
| MEAN | 6 | 20 | 34 | 55 | 54 |
| S.D. | 2.2 | 4.3 | 7.6 | 7.1 | 10 |

FIG. 35

| Time (Hrs) | Percent MTX Retained (Plasma) | Percent MTX Retained Liver | Percent MTX Retained PBS |
|---|---|---|---|
| 0 | 99.13 ± 0.63 | 99.0 ± 0.81 | 99.5 ± 0.55 |
| 0.5 | 97.12 ± 0.62 | 94.5 ± 2.08 | 98.5 ± 0.57 |
| 1.0 | 90.0 ± 1.32 | 93.2 ± 2.99 | 98.0 ± 0.82 |
| 2.0 | 90.7 ± 1.20 | 88.5 ± 1.91 | 97.5 ± 0.81 |
| 4.0 | 87.5 ± 1.40 | 84.5 ± 1.73 | 97.5 ± 1.15 |
| 8.0 | 84.5 ± 1.20 | 80.2 ± 1.26 | 97.3 ± 0.96 |
| 24 | 84.7 ± 1.10 | 77.5 ± 1.50 | 96.7 ± 0.95 |
| 48 | 83.7 ± 1.90 | 74.5 ± 1.20 | 96.5 ± 1.50 |
| 72 | 82.3 ± 1.80 | | 96.4 ± 1.29 |

FIG. 36

| GROUPS | I | II | III | IV | V | VI | Mean ± S.D |
|---|---|---|---|---|---|---|---|
| | (pg/mL) | | | | | | |
| Control | 25 | 21 | 13 | 21 | 12.9 | 18 | 18.5 ± 4.8 |
| Blank PLGA | 19.9 | 19.3 | 22.1 | 19.5 | 21.8 | 19.3 | 20.2 ± 1.1 |
| Blank Albumin | 25.7 | 20.3 | 51.0 | 20.9 | 21.6 | 21.4 | 22.0 ± 2.1 |
| MTX Solution (15 mg/kg) | 22.7 | 53.9 | 19.3 | 26.9 | 27.3 | 19.0 | 28.1 ± 11.1 |
| MTX-PLGA (15 mg/kg) | 19.9 | 16.6 | 26.4 | 24.4 | 61.9 | 48.0 | 33.1 ± 16.0 |
| MCSF Solution 100 µg/kg Q 3 days | 83.2 | 58.0 | 41.5 | 82.7 | 65.7 | 53.9 | 64.3 ± 16.5* |
| MCSF Albumin 100 µg/kg Q 3 days | 18.1 | 30.3 | 32.1 | 42.9 | 26.7 | 31.9 | 30.4 ± 8.1 |
| MCSF Solution 10 µg/kg | 68.0 | 41.2 | 26.9 | 26.4 | 35.8 | 24.0 | 37.1 ± 16.6 |
| MCSF Solution 100 µg/kg | 39.9 | 39.4 | 28.1 | 21.7 | 25.4 | 19.9 | 29.1 ± 8.7* |

FIG. 42

| GROUPS | I | II | III | IV | V | VI | Mean (pg/mL) | S.D. |
|---|---|---|---|---|---|---|---|---|
| MCSF Albumin 10 µg/kg | 31.1 | 22.2 | 29.1 | 24.9 | 25.6 | 35.3 | 28.1 | 4.7 |
| MCSF Albumin 100 µg/kg | 70.2 | 31.1 | 71.1 | 52.6 | 69.7 | 77 | 62 *,+ | 17.2 |
| Blank PLGA MCSF Albumin 100 µg/kg | 60.1 | 70.1 | 33.9 | 36.0 | 79.1 | 40.2 | 53.2 * | 19.3 |
| MCSF Solution 100 µg/kg MTX Solution 15 mg/kg | 28.7 | 36.2 | 59.6 | 21.6 | 23.0 | 49.9 | 37.3 | 14.1 |
| MCSF Solution 10 µg/kg MTX Solution 15 mg/kg | 25.4 | 25.7 | 23.3 | 22.4 | 24.9 | 23.0 | 24.1 | 1.38 |
| MCSF Albumin 100 µg/kg MTX Solution 15 mg/kg | 30.5 | 23.4 | 31.6 | 31.3 | 66.9 | 40.1 | 37.3 | 15.5 |
| MCSF Albumin 10 µg/kg MTX-PLGA 15 mg/kg | 22.1 | 41.9 | 55.8 | 32.4 | 23.5 | 24.5 | 33.4 | 13.3 |
| MCSF Albumin 100 µg/kg MTX-PLGA 15 mg/kg | 21.0 | 24.3 | 39.4 | 25.7 | 38.6 | 42.6 | 31.6 | 9.2 |

FIG. 43

| GROUPS | I | II | III | IV | V | VI | Mean pg/mL | S.D |
|---|---|---|---|---|---|---|---|---|
| Control | 41.1 | 23.5 | 34.2 | 23.2 | 35.2 | 31.7 | 31.5 | 7.02 |
| Blank PLGA | 30.6 | 30.9 | 32.9 | 30.8 | 31.1 | 31.6 | 31.3 | 1.9 |
| Blank Albumin | 37.0 | 35.5 | 32.4 | 34.6 | 60.2 | 33.1 | 38.8 | 10.6 |
| MTX Solution (15 mg/kg) | 45.3 | 41.6 | 35.9 | 41.0 | 30.9 | 41.0 | 37.6 | 6.02 |
| MTX-PLGA (15 mg/kg) | 33.9 | 28.9 | 41.3 | 38.6 | 47.9 | 48.3 | 39.8 | 7.6 |
| MCSF Solution 100 µg/kg Q 3 days | 60.9 | 72.8 | 93.7 | 144 | 85.5 | 77.9 | 89.2* | 29.2 |
| MCSF Albumin 100 µg/kg Q 3 days | 145 | 101 | 119 | 147 | 163 | 271 | 173* | 71.1 |
| MCSF Solution 10 µg/kg | 100 | 72.0 | 47.6 | 63.0 | 59.0 | 47.0 | 64.7* | 19.7 |
| MCSF Solution 100 µg/kg | 59.1 | 83.3 | 58.1 | 84.6 | 37.9 | 40.4 | 60.6* | 20.1 |

FIG. 44

| GROUPS | I | II | III | IV | V | VI | Mean (pg/mL) | S.D |
|---|---|---|---|---|---|---|---|---|
| MCSF Albumin 10 µg/kg | 53.8 | 49.4 | 45.6 | 42.4 | 61 | 38.9 | 50.6* | 7.5 |
| MCSF Albumin 100 µg/kg | 119 | 121 | 120 | 56.0 | 129 | 89.0 | 105* | 28 |
| Blank PLGA MCSF Albumin 100 µg/kg | 114 | 241 | 151 | 275 | 170 | 278 | 204* | 69 |
| MCSF Solution 100 µg/kg MTX Solution 15 mg/kg | 112 | 82 | 189 | 77 | 95 | 135 | 115* | 42 |
| MCSF Solution 10 µg/kg MTX Solution 15 mg/kg | 38.2 | 35.8 | 43.9 | 39.6 | 42 | 37.5 | 39.6+ | 3.1 |
| MCSF Albumin 100 µg/kg MTX Solution 15 mg/kg | 178 | 122 | 213 | 171 | 118 | 112 | 152* | 41 |
| MCSF Albumin 10 µg/kg MTX-PLGA 15 mg/kg | 224 | 129 | 208 | 162 | 265 | 162 | 191 *+ | 49 |
| MCSF Albumin 100 µg/kg MTX-PLGA 15 mg/kg | 213 | 243 | 115 | 209 | 272 | 176 | 204* | 54 |

FIG. 45

METHODS OF ADMINISTERING MICROENCAPSULATED MATERIALS FOR IMMUNE MODULATED DISEASES

This is a division, of application(s) Ser. No. 08/434,542, filed May 4, 1995 now U.S. Pat. No. 6,555,110.

CROSS-REFERENCE TO RELATED APPLICATION

This application is a divisional application of U.S. Ser. No. 08/434,542, filed May 4, 1995, which is a continuation-in-part application of U.S. Ser. No. 07/977,057, filed Nov. 16, 1992, now abandoned, both applications being incorporated by reference in their entirety and being commonly assigned to the assignee of the present invention.

FIELD OF THE INVENTION

The present invention relates generally to the field of drug delivery systems. More particularly, the present invention relates to a method for microencapsulating drugs using biodegradable nonantigenic materials and also to microencapsulated compositions that are targeted either to macrophages, other phagocytic cells of the immune system, or a diseased organ, which phagocytize the microspheres and digest the coating, releasing the intact drug or active fragment thereof intracellularly or at the site of attachment. Such compositions are useful in treating and preventing disease.

BACKGROUND OF THE ART

Drug delivery technology can bestow new leases on the lives of seemingly ineffective or inefficient drugs by targeting them specifically to sites of action. In this manner, unwanted systemic side effects are obviated and dose requirements are substantially reduced. Macrophage mediated delivery of drugs has been suggested as an alternative for treatment of several types of diseases. Modern immunology has acknowledged the importance of the monocyte and its mature counterpart, the macrophage as the prime antigen presenting cell in immune interactions. As an extension of this function it can be theorized that macrophages may be utilized to present immunoactive drugs to relevant components of the immune system such as lymphocytes in an effort to modulate their function.

Systemic elimination systems developed by the body to attack and eliminate foreign material include macrophages and Kupffer cells. For the purposes of the present invention the term macrophage includes Kupffer cells, when appropriate. Macrophages are cells widely distributed in many tissues of the body including lympho-hemopoietic organs, skin, gut, other portals of entry and the nervous system. They are found in direct contact with the blood (monocytes, sinus-lining Kupffer cells) or extravascular space, and undergo complex migrations as they enter tissues after production mainly within the bone marrow of the adult. As mobile and long-lived cells the mononuclear phagocytes play central roles as effector cells in inflammatory reactions and cell mediated immune responses. Monocytes produced in the bone marrow are released into the blood stream where they circulate with an estimated half life of 8–9 hours. Most experimental evidence indicates that the monocytes migrate into tissue to replace senescent tissue macrophages, and differentiate into cells of varied morphological and functional characteristics. Although definitive information on density and tissue distribution of these cells is still not available it is clear that the tissue content of mononuclear phagocytes, often associated with the vasculature greatly exceeds the bone marrow replicative pool. These cells, in a real sense are the first line of defense, followed by secondary waves of granulocytes, lymphocytes and monocytes from the circulation.

The term "activated macrophage" refers to cells with increased phagocytic activity, increased content of acid hydrolases, more active metabolism, and, more importantly, an increased microbicidal capacity. Macrophages become activated following specific immunity involving the T lymphocyte. The T lymphocyte represents the specific branch of the cellular response which, in some way or another (most likely via secretion of soluble products), activates macrophages. The activated macrophages display considerable enhancement in their capacity to curb bacterial growth. Although macrophage activation clearly follows immune activation of the T cells, it can also result from direct interaction of certain bacterial products or other chemicals with the macrophage. Unstimulated macrophages or non-activated macrophages generate low and variable cytokine activity. However, as with enzyme secretion, the secretion of these lymphocyte-stimulatory activities can be modulated. Two conditions produce an increase in activity: one is a phagocytic challenge, the second is exposure to activated T lymphocytes. Exposure of macrophages to bacteria, antigen-antibody complexes, latex beads, or endotoxin results in a marked increase (up to 10 times) in the activity tested, both in mitogenic response of the thymocytes and in antibody formation. This increase is seen for 1 to 2 days, and then decays away. The presence of activated T cells, which by themselves were not responsible for the activities, markedly enhances their production. The highest mitogenic activity found in cell culture results from the addition of a small number of the activated T cells to the macrophage culture.

The term phagocytosis is used to describe the internalization of large particles, such as those visible by light microscope, mostly viruses and bacteria. Uptake occurs by close apposition of a segment of plasma membrane to the particle's surface, excluding most if not all of the surrounding fluid. The phenomenon of phagocytosis seen in living cells in tissue culture or in-vivo has been well described. Phagocytosis is a process that occurs in three stages: attachment, ingestion, and digestion of the particles. The activated macrophage possessing a ruffled surface at the leading edge pushes out processes towards a particulate substance and rapidly flows around it. The entire process may only take a few minutes. Once ingested, the material may be totally digested, it may persist in the form of an indigestible residue, or it may actually fill up the whole cell, and if toxic may kill the cell. When the particle is too large for one cell to ingest, several cells flow around it and form a capsule. After ingestion, the vesicle which forms around the phagocytized particle, the phagosome fuses with one or more lysosomes to form a secondary lysosome or phagolysosome. The lysosome is a membranous bag of hydrolytic enzymes to be used for the controlled intracellular digestion of ingested materials. The hydrolytic enzymes contained in the lysosome are thus discharged into the enlarged vacuole to degrade the contents.

The deleterious effects of immune modulated diseases that manifest themselves due to improper recognition of "self" from "non-self" may be effectively reduced using this mode of drug delivery. Rheumatoid arthritis (RA) is one such disease affecting a large percent of the geriatric population. And while macrophages may not be a primary target for the virus causing acquired immune deficiency syndrome (AIDS), they have been implicated as carriers of the virus.

Cytokines are polypeptide hormones which have a variety of physiologic activities intended to "up-regulate" and/or "down-regulate" the immune system.

The cytokine cascade, although not fully elucidated, involves the release of a number of molecules, including tumor necrosis factor alpha (TNFa), interleukin-1 beta (IL1β), interleukin-2 (IL2), interleukin-6 (IL6), interleukin-8 (IL8), colony stimulating factors (CSF), interferons (IFN), interleukin-1 receptor antagonist (IL1-ra) as well as other interleukins whose function is still not completely understood from monocytes, macrophages, lymphocytes, and other tissues throughout the body. These cytokines act both locally and systemically to recruit other white blood cells to the site of infection, activate macrophages, increase antibody production, produce fever, hyperlipidemia, hyperglycemia, and directly activate natural killer and lymphokine activated killer lymphocytes thereby destroying tumor cells. In cancer patients, the concentration of cytokines such as tumor necrosis factor alpha (TNFa) and interleukin-1 beta (IL1-β) have been observed to be decreased during active tumor growth. Administration of macrophage/immune activators such as microencapsulated macrophage colony stimulating factor have been shown to reduce cancer mortality and lead to increases in local TNFa and IL1β concentration. Alternatively, administration of microencapsulated TNFa and IL1β may activate cellular immunity and increase tumoricidal activity of T-lymphocytes through upregulation of macrophage induced T-cell clonal expansion.

Although this response is usually beneficial, during overwhelming sepsis or other immune response challenges a hyper-responsiveness of cytokines has been shown to produce lethal effects. Massive vascular permeability leads to cardiovascular collapse and pulmonary edema. Coagulation defects may also complicate the clinical condition adding to increased mortality. It has been demonstrated in several animal models that the pre-treatment and continued intravenous administration of monoclonal antibodies (MAB's) or polyclonal antibodies (PAB's) to TNFa or IL1-ra can attenuate the clinical syndrome of sepsis and prevent mortality from lethal injections of live bacteria.

The use of intravenously administered MAB's to cytokines have been reported in the scientific literature for the prevention of mortality from experimental septic or endotoxemic shock since 1987. Typical experiments have used monoclonal antibodies, such as those to TNFa, administered directly to a subject concomitant with a dose of bacteria or other source of immunogenic challenge.

There are several potential problems with the direct administration of high, frequent does of MAB's for systemic inhibition of cytokines. Although animal models provide an in vivo system to test a septic/endotoxemic model, sepsis in humans is sudden in onset and originates from a localized infection site rather than by an intravenous challenge. The current method of administration requires an antigen-antibody reaction with the cytokine in systemic circulation (i.e., after synthesis and release by the macrophage). Since intravenous MAB's can inactivate systemic cytokines, there is a potential for intravenous MAB's to inhibit the autocrine up-regulation of further cytokine synthesis and release by activated macrophages and lymphocytes. However, it is doubtful that unencapsulated MAB's can gain sufficient access to the macrophage localized at the site of infection to prevent release of the cytokines. Furthermore, MAB's administered systemically typically are metabolized before they reach the desired site.

Prior art efforts to target delivery of MAB's for reduction of inflammatory response have yet to effectively deliver the molecules into the macrophage to the area of localized infection or immune response, where cytokine production is initiated. Other immunologic pathogenic responses such as lupus, organ transplant rejection, and glomerulonephropathies have been shown to have localized cytokine production as the major cause of tissue inflammation and ultimate destruction of the organ involved.

Since reduction in cytokine response has been shown to lead to a decrease in the severity of several diseases, it would be desirable to have a targeted drug delivery system that would act intracellularly at a targeted site, rather than systemically. Such a system would utilize an encapsulating material that is recognizable by the uptake cell and be transported intracellularly where it would release the encapsulated drug into the cytoplasm.

It is therefore a principal object of the present invention to provide a delivery system for drugs and other molecules for cellular uptake (e.g., macrophages and Kupffer cells).

It is a further object of the present invention to provide a delivery system using albumin as an encapsulating material to coat a drug such that when administered in. vivo the microsphere will be ingested by a macrophage, resulting in the digestion of the albumin and the release of the drug or an active form or fragment of the drug intracellularly.

It is another object of the present invention to provide a method for treating an immune modulated disease comprising administering to a subject a preparation containing pharmaceutically acceptable carrier and a biodegradable microsphere containing a neutralizing antibody to a cytokine.

As an example of the use of a drug as an immunosuppressant, Cyclosporin A (CsA) (Sandimmune, Sandoz) has gained wide acceptance by most transplant physicians as the immunosuppressant of choice for preventing rejection of solid organ grafts and graft-versus-host disease. The drug has a specific effect on T-lymphocytes in which it seems to prevent the transcription of genes for several lymphokines. The reduction in IL-2 prevents the clonal expansion of T-lymphocytes and their differentiation into effector T-cells. The reduction in IFN-tau interrupts the feedback mechanism between T-cells and macrophages and the aberrant expression of major histocompatibility complex (MHC) class II molecules. Through these mechanisms CsA exerts an immunosuppressive and anti-inflammatory effect.

Considerable evidence has accumulated to suggest that rheumatoid arthritis (RA) is an auto-immune disease. Activated T-lymphocytes interrelate with macrophages, other inflammatory cells and effector cells in joint tissue, leading to symptoms of inflammation accompanied by joint destruction. Immunosuppressive treatment is already well established in this disease and several trials have already taken place using CsA. A review of studies concludes that CsA is efficacious in controlling inflammatory and functional symptoms, although this improvement is not generally accompanied by reductions in erythrocyte sedimentation rate (ESR) and rheumatoid factor. The frequency of adverse events is comparable to that of other treatments but nephropathy remains the principal factor limiting the use of CsA. Recent evidence suggests that with a strict dosage strategy and good monitoring this problem is controllable and reversible.

Studies have also shown that CsA is capable of inhibiting both adjuvant arthritis and collagen arthritis in rats when administered at the time of disease induction. The effects, however, on established arthritis in these animals appear to be different depending on the animal model. Toxicity is another major concern associated with the use of CsA. Nephrotoxicity, hepatotoxicity, hirsutism, neurotoxicity, hypertension and altered coagulability have all been reported with CsA. In RA patients treated with CsA, those adverse effects that are the most prevalent include nephrotoxicity, hypertension, gastrointestinal intolerance, hypertrichosis and tremors due to high systemic levels of CsA. Recent reports indicate that the clearance of CsA is decreased in animals models of arthritis and diabetes. Therefore, when treating RA patients with CsA, the dose and blood levels of this drug should be carefully monitored because of drug toxicity, and because of the effect of the disease state on the disposition of the drug. A targeted microsphere system employing subtherapeutic doses of CsA would be desirable in order to overcome the limitations of systemic, nonspecific delivery of CsA. Other immunologically mediated diseases such as glomerulonephritis, organ transplant rejection, and lupus would likely benefit from a similar application of microencapsulated immunosuppressive agents.

Prior art encapsulation techniques have been directed at sustained release of an encapsulated drug using a selectively permeable coating or membrane through which the drug dissolves or otherwise passes. Numerous patents and articles describe the encapsulation of a variety of molecules, including drugs, vitamins, hormones, steroids, viruses, and other compositions, by an equally numerous variety of coatings or membrane materials. For instance, U.S. Pat. No. 5,017,379 describes antifibrin antibodies encapsulated in a biodegradable microcontainer which are released at the site of a targeted blood clot in an artery or vein. U.S. Pat. No. 4,925,661 discloses a method of delivering cytotoxic reagents, such as the A fragment of the diphtheria toxin, to cells by encapsulating the toxin in an immunoliposome composed from phosphatidylethanolamine and oleic acid in a molar ratio of 8:2 and a fatty acid derived antibody.

SUMMARY OF THE INVENTION

The present invention relates generally to an improved drug delivery system for modulating immune response by modifying cytokine response in macrophages. More particularly, a composition is disclosed for use in a drug delivery system comprising a drug microencapsulated with a biodegradable nonantigenic substance that can be recognized, phagocytosed and uncoupled by macrophages. In a preferred embodiment, the present invention provides a anticytokine neutralizing antibody (NA) that is encapsulated with albumin to form a microsphere. The microsphere is formulated into an injectable or otherwise administrable preparation that can be administered in vivo. Once administered the microspheres are recognized and attacked by macrophages and ingested by phagocytosis. Once inside the macrophage enzymes digest the albumin, releasing the NA or an active form or fragment of the NA into the cell interior. NA may bind to cytokine receptors or translated cytokines inhibiting further activity. Microencapsulation techniques presented herein may also be used to target the macrophage with other agents such as proteases or anti-retroviral agents used to treat other illnesses which as systemic in nature. Diseases such as septic shock, which result from a massive immune reaction from invasion by bacteria, fungi, or bacteria-produced endotoxin or exotoxins, can be effectively. treated by this composition.

A potential mechanism of action of microencapsulated NA on endotoxin or bacteria stimulated cytokine release involves the following steps and is depicted in FIG. 1. Step 1: Endotoxin/bacteria are either phagocytized or bind to the macrophage. Step 2: The organism/product transduces a signal to the nucleus stimulating transcription and translation of TNFa, IL-1β, IL-6 and IL-8. Step 3: TNFa is synthesized and released into the cell where it can either be secreted or re-stimulate the nucleus to produce additional cytokines (autocrine). Step 4: Phagocytized microcapsules of NA are uncoupled by lysosomal enzymes and the active $F(ab)^2$ fragments bind to the intracellular cytokine inhibiting both autocrine up-regulation and release of the active cytokine. Binding of TNF-NA or IL1-NA may reduce related cytokines through an inhibition of nuclear stimulated cytokine synthesis (see Step 5) or by binding prevent released cytokine from binding to extracellular receptors (see Step 7), which has been shown to occur in vivo. Step 5: TNFa, IL-1, and IL-6 have been shown in vivo to stimulate synthesis and release of each other probably by nuclear up-regulation of cytokine synthesis. Step 6: Released, unbound cytokines can stimulate effector organs as well as bind to lymphocytes and other white cells stimulating further production of cytokines. Step 7: Cytokine binding of receptors of macrophages and other white cells can lead to an increase in cellular synthesis and release of cytokines. Step 8: Membrane bound cytokines stimulate nuclear synthesis of all the cytokines in the cascade. Summary: Microencapsulated anticytokine antibodies may exhibit their effect on cytokine release by acting at Steps 3 and 5 and therefore blunt further release at Steps 6, 7, and 8.

The present invention also may be particularly useful in treating rheumatoid arthritis, AIDS, uveitis, psoriasis, arthritis, diabetes, asthma, organ transplant rejection, lupus, tumor regression, viral infections, renal disease such as glomerulonephropathies, presentation of vaccines and adjuvants, myasthenia gravis and other immune modulated conditions.

Albumin or globulin is the preferred material used to encapsulate water soluble molecules, such as anticytokine NA, peptides, insulin, proteins, drugs and the like. In an alternative embodiment, poly DL(lactic co-glycolic acid) (PLGA), a linear polyester that breaks down to D-lactic acid, L-lactic acid and glycolic acid, is used to encapsulate water insoluble molecules, such as vitamins and many drugs.

In another aspect of the present invention, a method is presented for preparing the encapsulated drug, comprising dissolving albumin in water or phosphate buffered saline (PBS); separately solubilizing NA in PBS; mixing the two solutions together; cooling the mixture; adding the mixture to an amount of olive oil previously cooled, emulsifying the mixture to form microspheres; crosslinking the microspheres by adding a solution of glutaraldehyde and stirring while maintaining the cool temperature of the mixture; washing the microspheres; sizing the microspheres; and drying the microspheres.

BRIEF DESCRIPTION OF THE DRAWINGS

FIG. 1 illustrates a potential mechanism of how microencapsulated neutralizing antibody act in vivo.

FIG. 2 shows a graph of cumulative percent radiolabel released versus time for 99mTc radiolabeled microspheres in PBS, culture medium and rat plasma. The radiolabel studies were conducted in phosphate buffered saline, culture medium and rat plasma. Error bars represent means±sem. Key: °=PBS; square=Culture Medium; triangle=plasma.

FIG. 3 is an in vitro cyclosporin dissolution study and shows a chart of cumulative percent cyclosporin A release versus time. Values are means±sem of six samples.

FIG. 4 shows 99mTc-PLGA microsphere uptake profiles of normal and arthritic macrophages in vitro. Key: Open circle=normal macrophages; closed circle=arthritic macrophages.

FIG. 5 shows a lymphocyte transformation study protocol, wherein all groups were harvested at 72 hours.

FIGS. 6A and 6B show charts of the effect of various pretreatments on transformation of normal lymphocytes after addition of thymidine at 24 hours. In FIG. 6A, Key: Open circle=10:1 Microsphere:Mo (Monoclonal antibody); open square=5:1 Microsphere:Mo; open triangle=1:1 Microsphere:Mo. Each pretreatment was significantly different from corresponding arthritics at each time (ANOVA, $p<0.05$). FIG. 6B shows microsphere uptake by normal and arthritic macrophages; Key: Closed circle=10:1 Microsphere:Mo (Significantly different from other does at each time (ANOVA Repeated measures, $p<0.05$); closed square=5:1 Microsphere:Mo; closed triangle=1:1 Microsphere:Mo; *=Significantly different from other doses at 15 minutes (ANOVA, $p<0.05$).

FIGS. 7A and 7B show a chart of the effect of various pretreatments on transformation of arthritic lymphocytes after addition of thymidine at 24 hours using normal and arthritic cells (means sem). In FIG. 7A, Key: Star= significantly different from corresponding arthritic cells ($p<0.05$). In FIG. 7B, Key: Star=significantly different from corresponding normal cells ($p<0.05$);=significantly different from other groups in this study ($p<0.05$).

FIGS. 8A and 8B show plasma or serum cyclosporin A levels in arthritic rats. FIG. 8A shows paw volume changes of untreated controls and treated arthritic rats after CsA micropheres 1 mg/kg once. Key: Closed circle=left paw treated; closed square=right paw treated; open circle=left paw untreated; open square=right paw untreated. FIG. 8B shows paw volume changes of untreated arthritic controls and arthritic rats treated with SANDIMMUNE® 1 mg/kg/2 days i.p.

FIG. 9 shows the inhibition of TNFα following in vitro administration of anticytokine antibodies. Key: +=blank microcapsule without any neutralizing antibody or endotoxin (negative control); star=blank microcapsule and E. coli endotoxin (positive control); closed square= microencapsulated TNFα neutralizing antibody; x=microencapsulated IL1β neutralizing antibody.

FIG. 10 shows the inhibition of IL1β following in vitro administration of anticytokine antibodies. Key: +=blank microcapsule without any neutralizing antibody or endotoxin (negative control); star=blank microcapsule and E. coli endotoxin (positive control); closed square= microencapsulated TNFα neutralizing antibody; x=microencapsulated IL1β neutralizing antibody; diamond= microencapsulated IL8 neutralizing antibody; triangle= microencapsulated IL1-receptor antagonist; hourglass= microencapsulated IL6 neutralizing antibody.

FIG. 11 shows the inhibition of IL6 following in vitro administration of anticytokine antibodies. Key: +=blank microcapsule without any neutralizing antibody or endotoxin (negative control); star=blank microcapsule and E. coli endotoxin (positive control); closed square= microencapsulated TNFα neutralizing antibody; x=microencapsulated IL1β neutralizing antibody; triangle= microencapsulated IL1-receptor antagonist; hourglass= microencapsulated IL6 neutralizing antibody.

Figure 17:
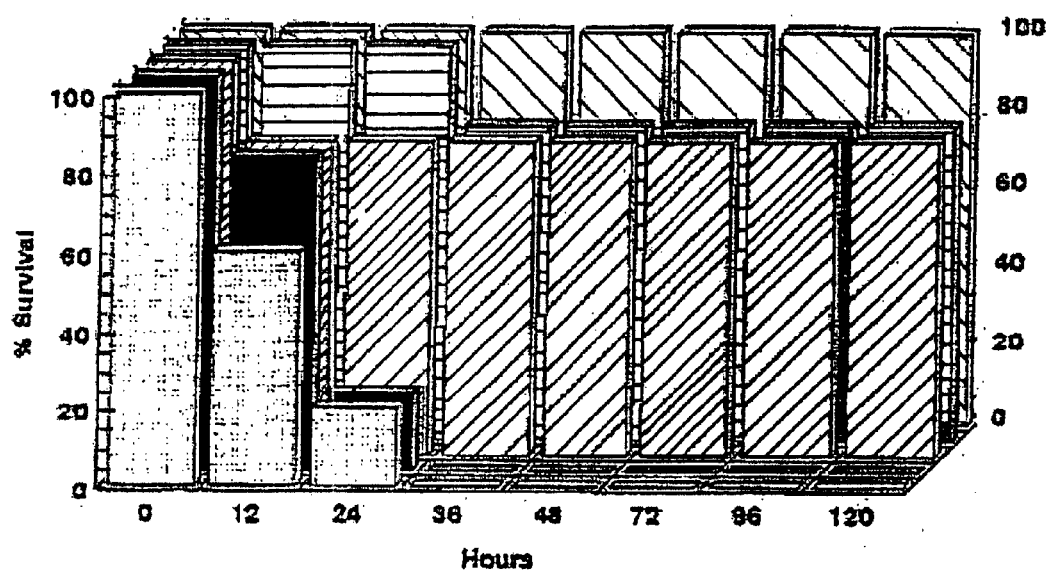

FIG. 17 is a graph of the survival of rats following a lethal endotoxin challenge with or without microencapsulated TNFa, IL1β, or TNFa+IL1β antibodies. Key: Dotted bar= endotoxin ("ET") only; black bar=endotoxin and blank microcapsule without any neutralizing antibody ("NAS") or endotoxin; light grey bar=IL1/TNF monoclonal neutralizing antibody; darker grey bar=IL1 monoclonal neutralizing antibody; darker grey bar=TNF monoclonal neutralizing antibody. [ET vs TNF NA $P<0.004$ (Fisher's); ET vs IL-1 and IL-1/TNF NA $P<0.024$ (Fisher's); and ET vs blank (NS); NA vs NA (NS).

Figure 18:
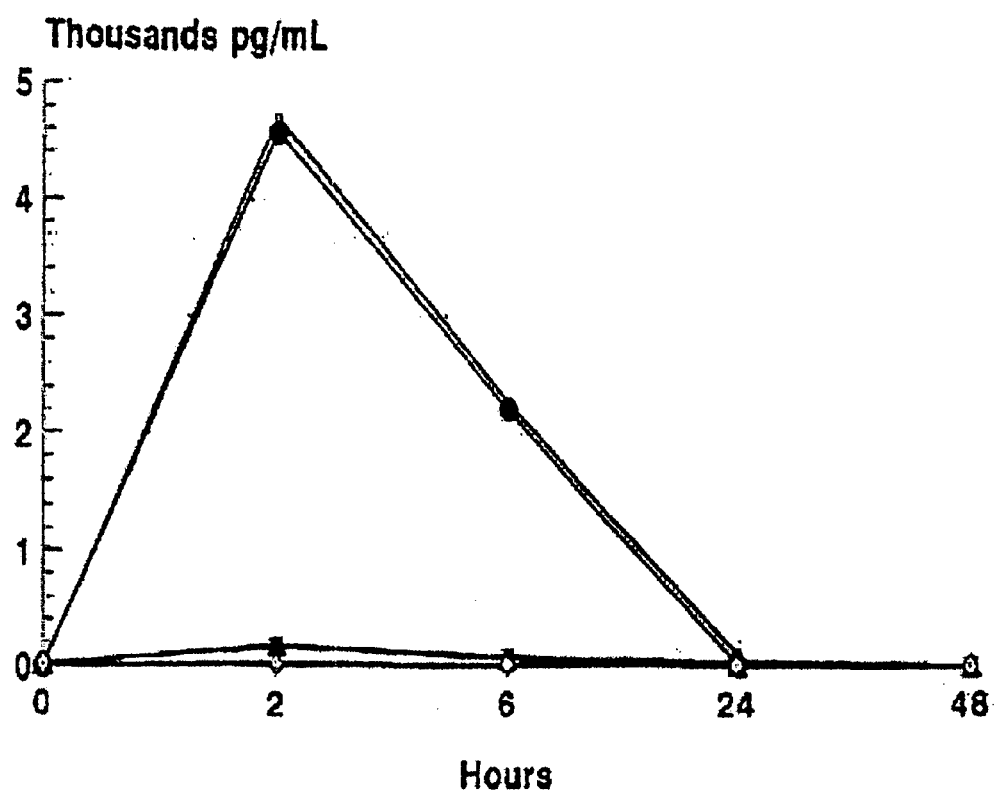

FIG. 18 is a graph of the TNFa concentration following a lethal endotoxin challenge with or without microencapsulated TNFa, IL1β, or TNFa+IL1β antibodies. Key: Diamond=TNF/IL-1 monoclonal neutralizing antibody; triangle=TNF monoclonal neutralizing antibody; square= IL-1 monoclonal neutralizing antibody; large circle= endotoxin only; small square=endotoxin and blank microcapsule.

Figure 19:
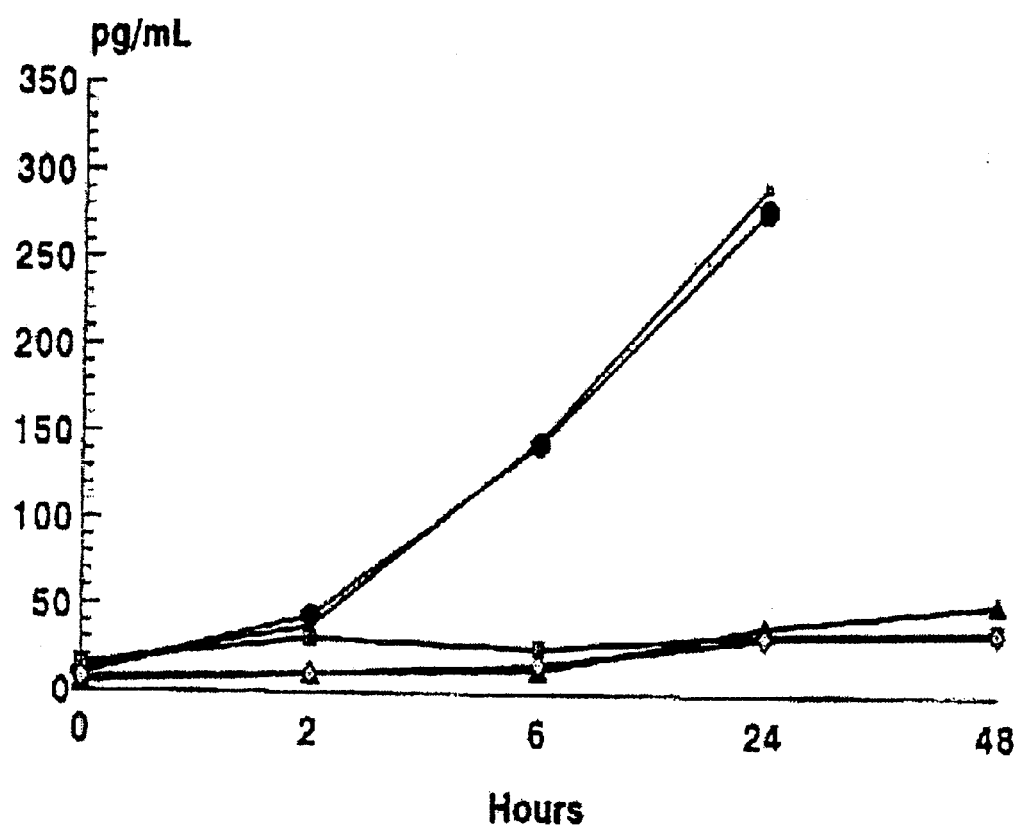

FIG. 19 is a graph of the IL1β concentration following a lethal endotoxin challenge with or without microencapsulated TNFa, IL1β, or TNFa+IL1β antibodies. Key: Diamond=TNF/IL-1 monoclonal neutralizing antibody; triangle=TNF monoclonal neutralizing antibody; square= IL-1 monoclonal neutralizing antibody; large circle= endotoxin only; small square=endotoxin and blank microcapsule.

FIG. 20 is a table of the percent survival of rats treated simultaneously with bacteria, microencapsulated neutralizing antibodies, unencapsulated neutralizing antibodies, with or without antibiotics. Key: §=$P<0.05$ from monoclonal neutralizing antibody.

FIG. 21 is a table of the percent survival of rats treated simultaneously with bacteria, microencapsulated neutralizing antibodies, unencapsulated neutralizing antibodies, with or without antibiotics. Key: §=$P<0.05$ from monoclonal neutralizing antibody plus antibiotics.

FIG. 22 is a table of the percent survival of rats treated with bacteria, and then following a 4 hour delay microencapsulated neutralizing antibodies, unencapsulated neutralizing antibodies, with or without antibiotics. Key: §=$P<0.05$ from monoclonal neutralizing antibody plus antibiotics.

FIG. 23 is a table of the percent survival of rats treated with bacteria, and then following a 4 hour delay microencapsulated neutralizing antibodies, unencapsulated neutralizing antibodies, with or without antibiotics. Key: §=$P<0.05$ from monoclonal neutralizing antibody plus antibiotics.

Figure 24:
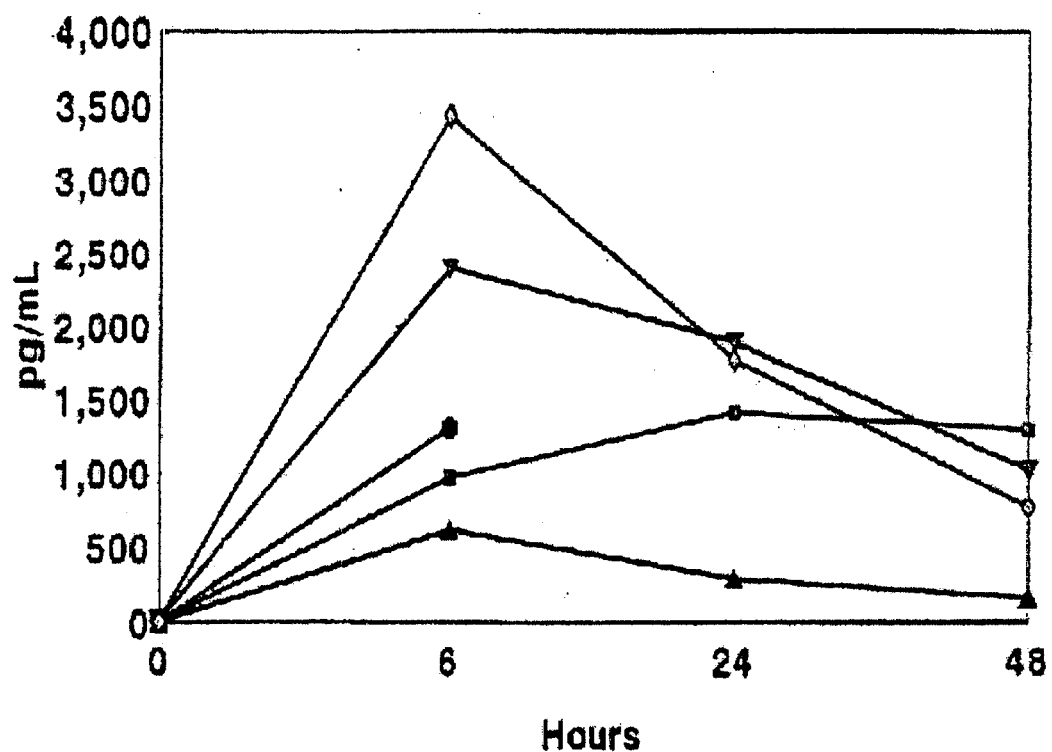

FIG. 24 is a graph of TNFa following simultaneous treatment with bacteria and microencapsulated neutralizing antibodies, unencapsulated neutralizing antibodies, with or without antibiotics. Key: §=$P<0.05$ from monoclonal neutralizing antibody plus antibiotics; *=$P<0.05$ from antibiotics alone; diamond=bacteria plus antibiotics (20%); large circle=bacteria plus neutralizing antibody solution (0%); black triangle=bacteria plus monoclonal neutralizing antibody plus antibiotics (100%); grey inverted triangle=bacteria plus neutralizing antibody solution plus antibiotics (0%); square=bacteria plus monoclonal neutralizing antibody (70%).

Figure 25:
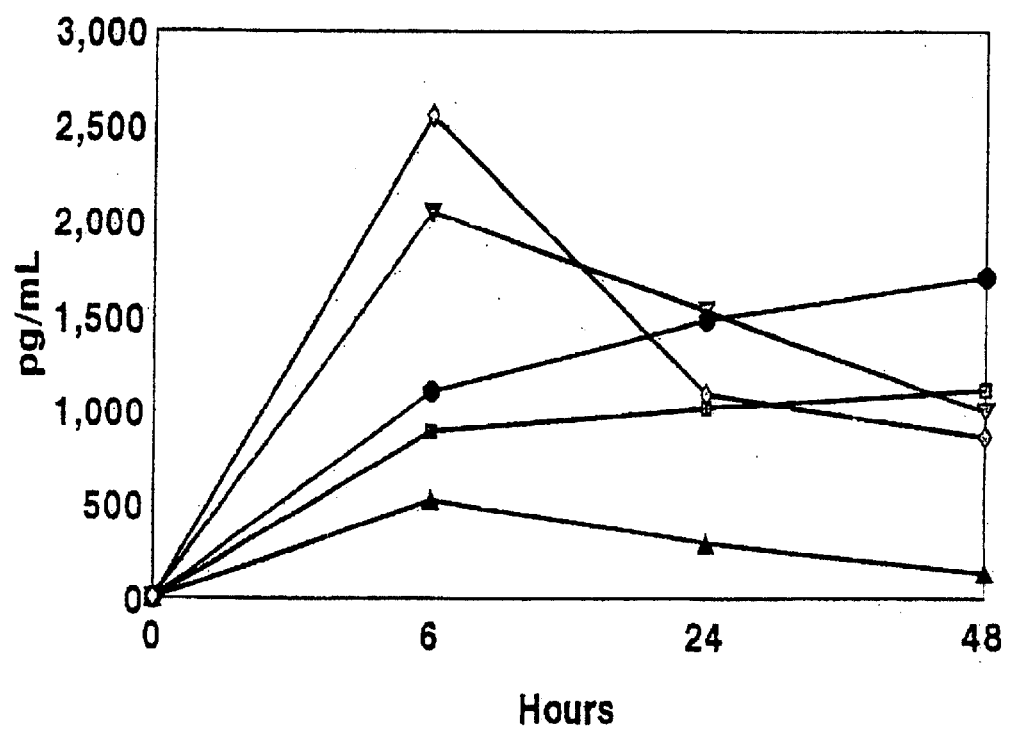

FIG. 25 is a graph of TNFa following simultaneous treatment with bacteria and microencapsulated neutralizing antibodies, unencapsulated neutralizing antibodies, with or without antibiotics. Key: §=P<0.05 from monoclonal neutralizing antibody plus antibiotics; *=P<0.05 from antibiotics alone; diamond=bacteria plus antibiotics (10%); large circle=bacteria plus neutralizing antibody solution (20%); black triangle=bacteria plus monoclonal neutralizing antibody plus antibiotics (100%); grey inverted triangle=bacteria plus neutralizing antibody solution plus antibiotics (20%); square=bacteria plus monoclonal neutralizing antibody (40%).

Figure 26:
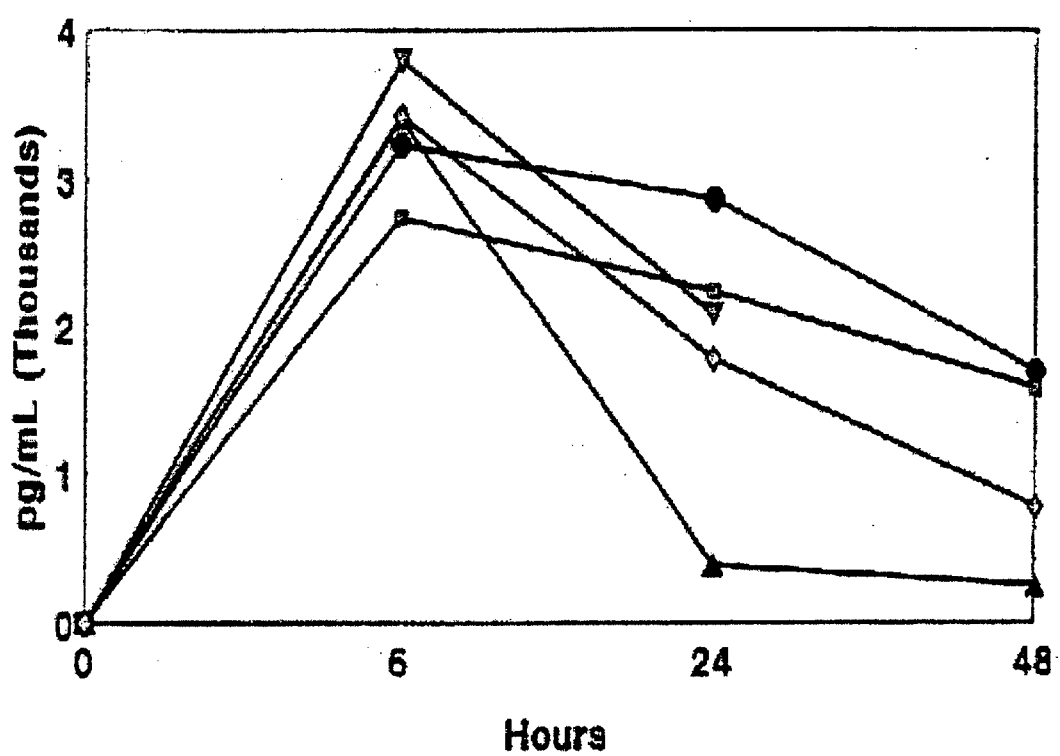

FIG. 26 is a graph of TNFa following delayed treatment with bacteria and microencapsulated neutralizing antibodies, unencapsulated neutralizing antibodies, with or without antibiotics. Key: diamond=bacteria plus antibiotics (20%); large circle=bacteria plus neutralizing antibody solution (10%); black triangle=bacteria plus monoclonal neutralizing antibody plus antibiotics (100%); grey inverted triangle=bacteria plus neutralizing antibody solution plus antibiotics (0%); square=bacteria plus monoclonal neutralizing antibody (20%).

Figure 27:
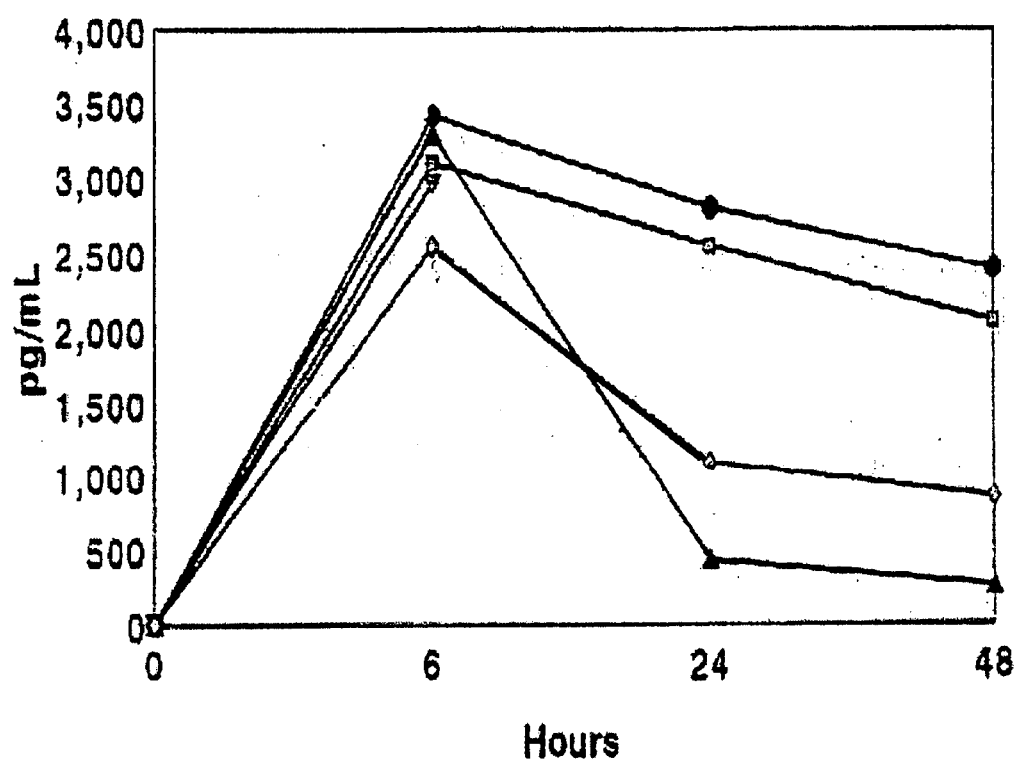

FIG. 27 is a graph of TNFa following delayed treatment with bacteria and microencapsulated neutralizing antibodies, unencapsulated neutralizing antibodies, with or without antibiotics. Key: diamond=bacteria plus antibiotics (10%); large circle=bacteria plus neutralizing antibody solution (20%); black triangle=bacteria plus monoclonal neutralizing antibody plus antibiotics (100%); grey inverted triangle=bacteria plus neutralizing antibody solution plus antibiotics (0%); square=bacteria plus monoclonal neutralizing antibody (0%).

Figure 28:
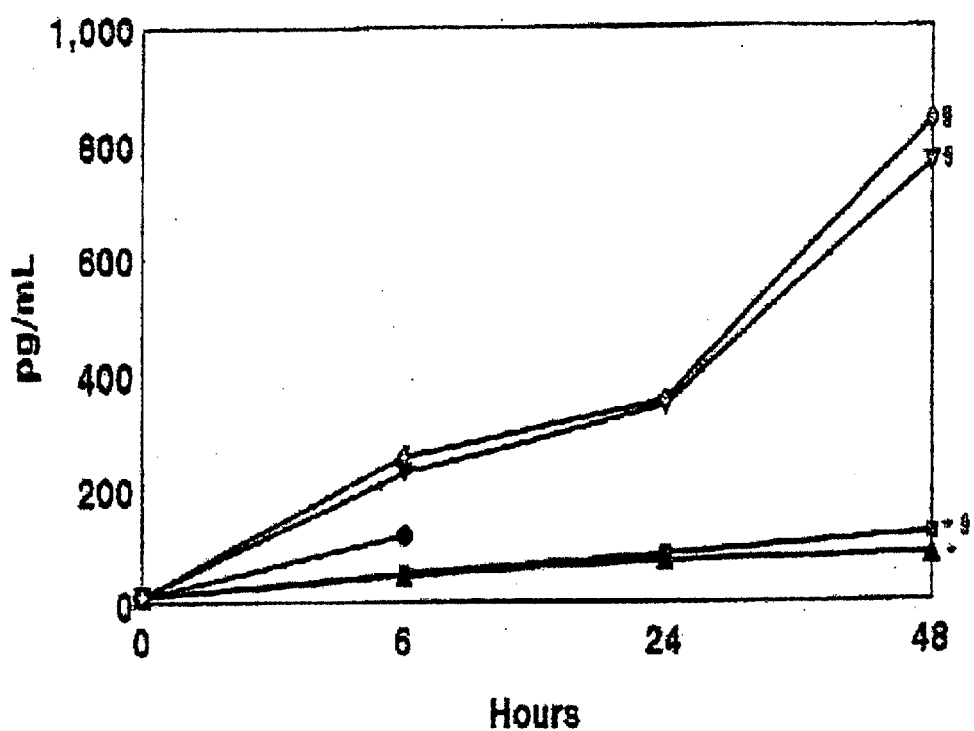

FIG. 28 is a graph of IL1$\beta$ following simultaneous treatment with bacteria and microencapsulated neutralizing antibodies, unencapsulated neutralizing antibodies, with or without antibiotics. Key: diamond=bacteria plus antibiotics (20%); large circle=bacteria plus neutralizing antibody solution (0%); black triangle=bacteria plus monoclonal neutralizing antibody plus antibiotics (100%); grey inverted triangle=bacteria plus neutralizing antibody solution plus antibiotics (0%); square=bacteria plus monoclonal neutralizing antibody (70%).

Figure 29:
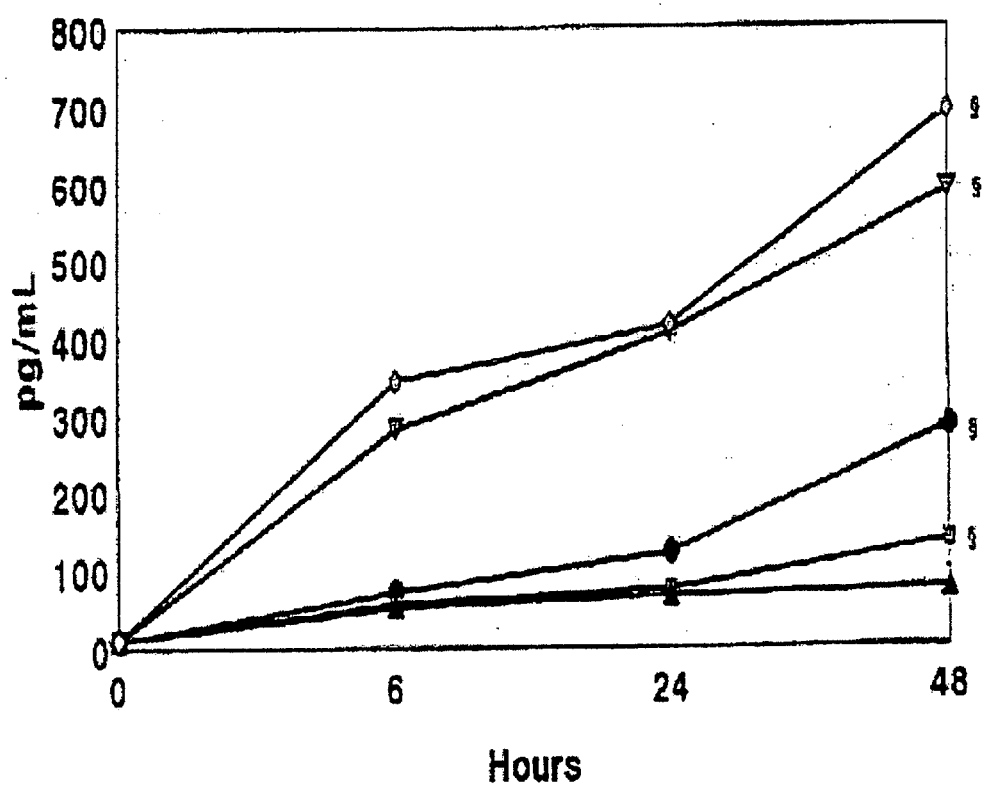

FIG. 29 is a graph of IL1$\beta$ following simultaneous treatment with bacteria and microencapsulated neutralizing antibodies, unencapsulated neutralizing antibodies, with or without antibiotics. Key: diamond=bacteria plus antibiotics (10%); large circle=bacteria plus neutralizing antibody solution (20%); black triangle=bacteria plus monoclonal neutralizing antibody plus antibiotics (100%); grey inverted triangle=bacteria plus neutralizing antibody solution plus antibiotics (20%); square=bacteria plus monoclonal neutralizing antibody (40%).

Figure 30:
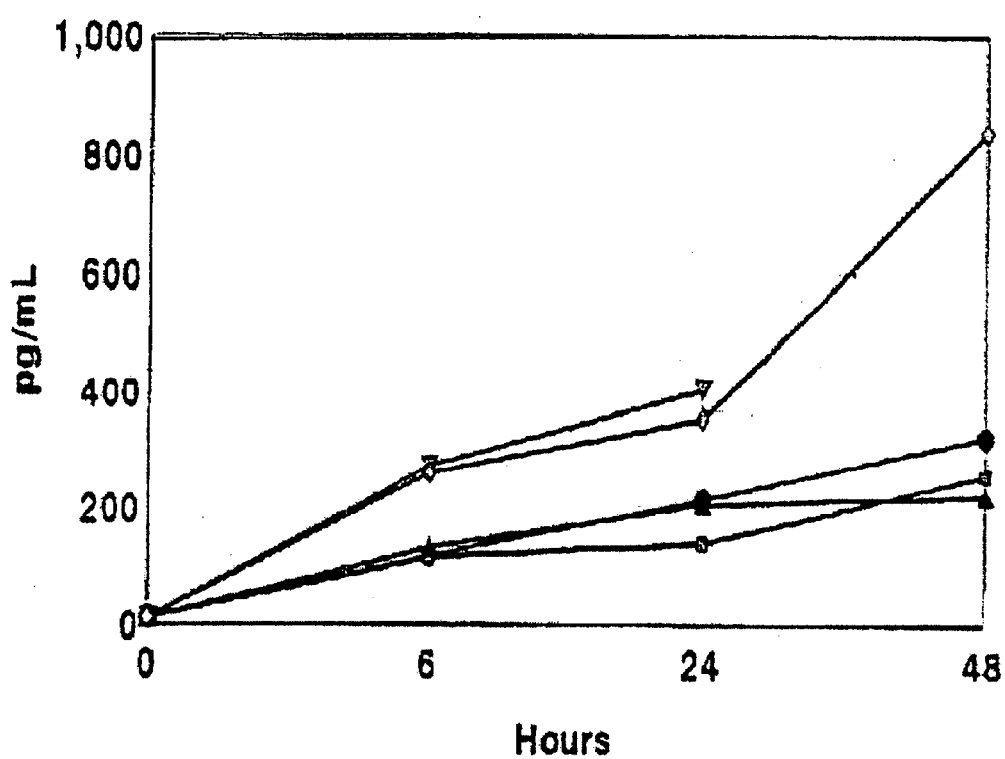

FIG. 30 is a graph of IL1$\beta$ following delayed treatment with bacteria and microencapsulated neutralizing antibodies, unencapsulated neutralizing antibodies, with or without antibiotics. Key: diamond=bacteria plus antibiotics (20%); large circle=bacteria plus neutralizing antibody solution (10%); black triangle=bacteria plus monoclonal neutralizing antibody plus antibiotics (100%); grey inverted triangle=bacteria plus neutralizing antibody solution plus antibiotics (0%); square=bacteria plus monoclonal neutralizing antibody (20%).

Figure 31:
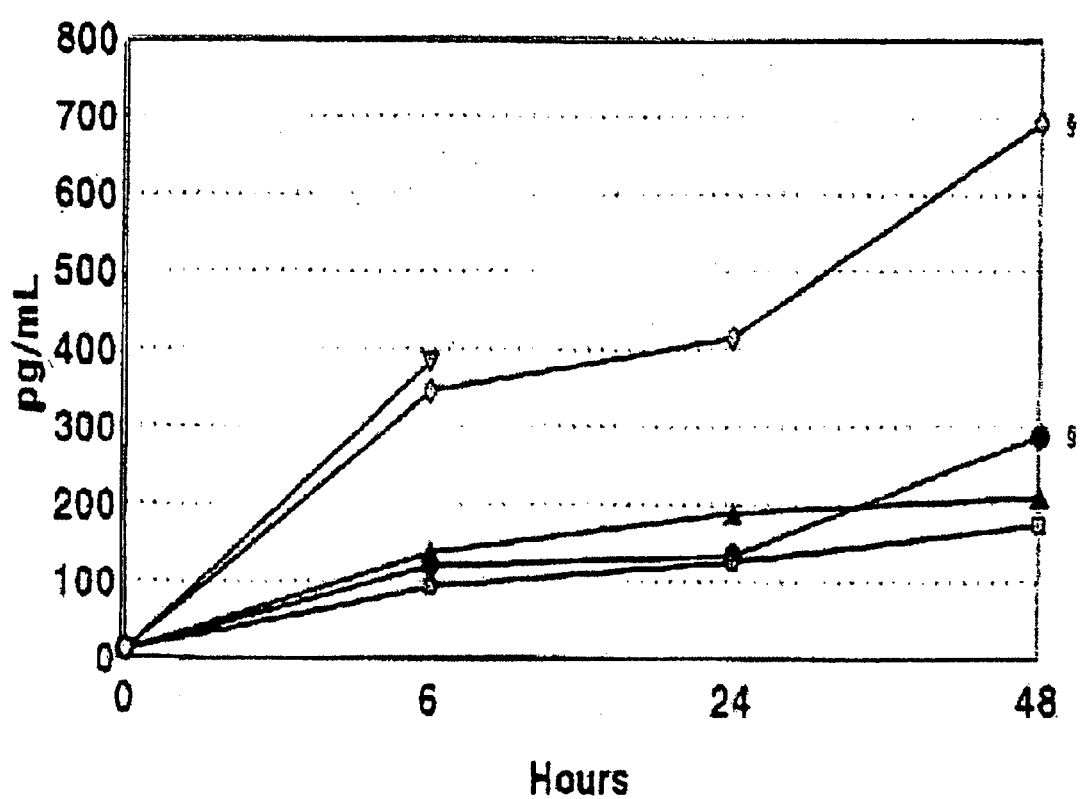

FIG. 31 is a graph of IL1$\beta$ following delayed treatment with bacteria and microencapsulated neutralizing antibodies, unencapsulated neutralizing antibodies, with or without antibiotics. Key: diamond=bacteria plus antibiotics (10%); large circle=bacteria plus neutralizing antibody solution (20%); black triangle=bacteria plus monoclonal neutralizing antibody plus antibiotics (100%); grey inverted triangle=bacteria plus neutralizing antibody solution plus antibiotics (0%); square=bacteria plus monoclonal neutralizing antibody (0%).

Figure 32:
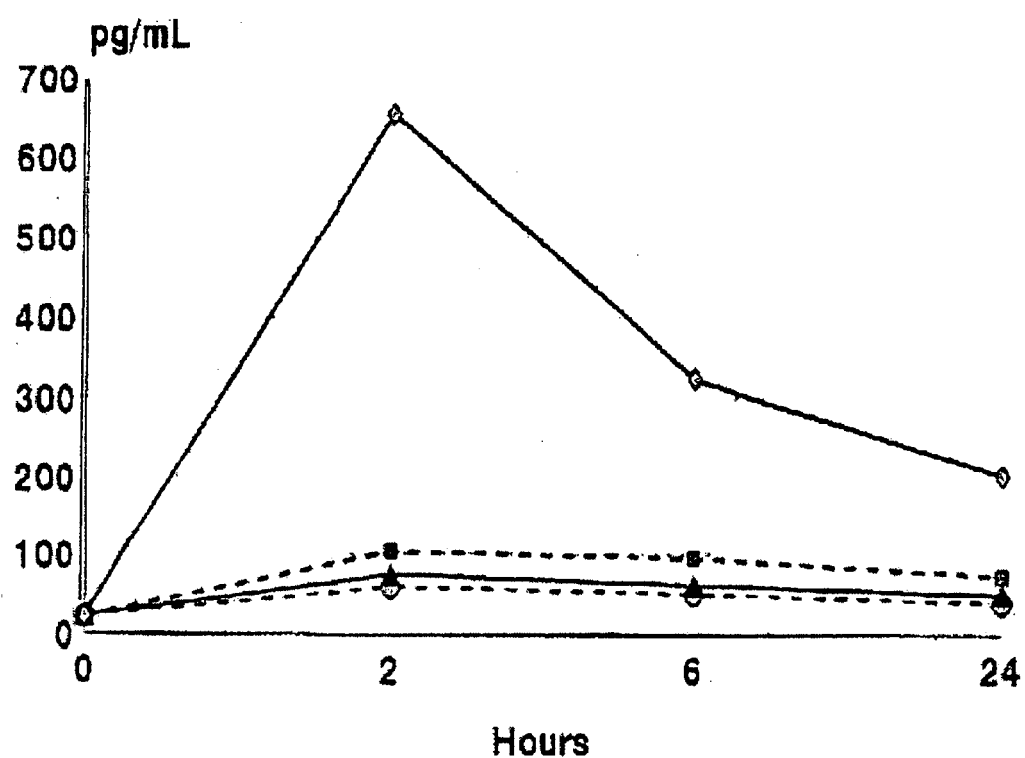

FIG. 32 is a graph of TNFa concentration following the administration of OKT3 and with microencapsulated TNFa, IL1$\beta$, or IL1+TNF neutralizing antibodies. Key: Diamond=OKT3 1 mcg/ml; triangle=TNF neutralizing antibody; square=IL1 neutralizing antibody; circle=TNF plus IL1 neutralizing antibody. [89% decrease in peak P<0.0001]

Figure 33:
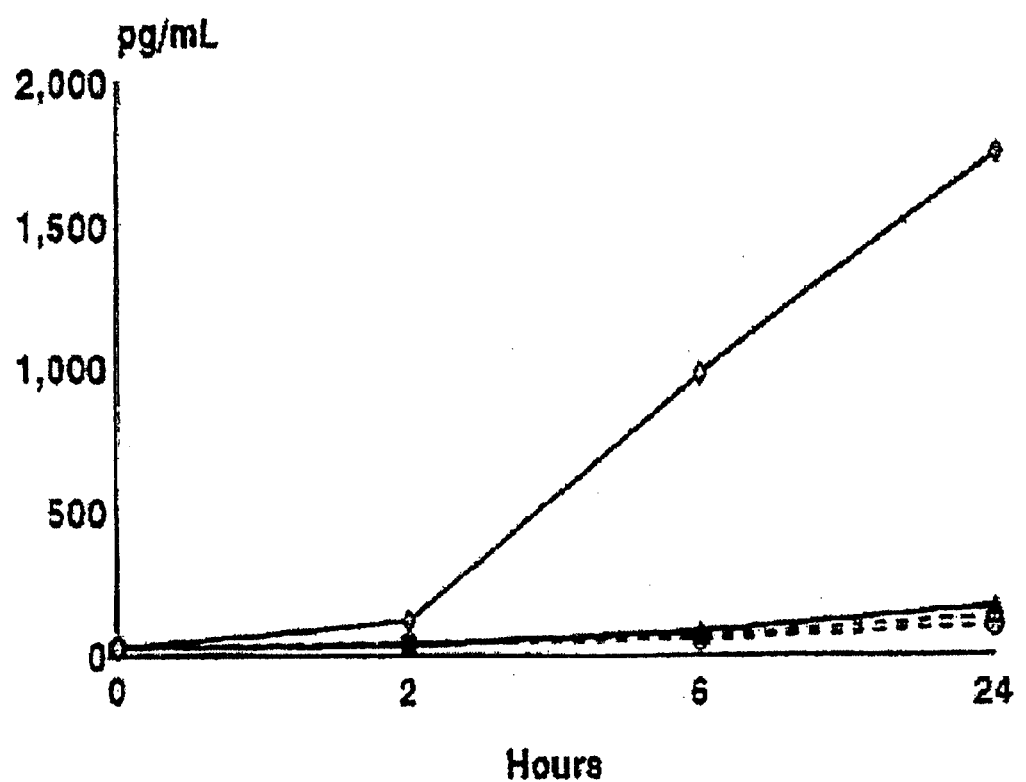

FIG. 33 is a graph of IL1$\beta$ concentration following the administration of OKT3 and with microencapsulated TNFa, IL1$\beta$, or IL1+TNF neutralizing antibodies. Key: Diamond=OKT3 1 mcg/ml; triangle=TNF neutralizing antibody; square=IL1 neutralizing antibody; circle=TNF plus IL1 neutralizing antibody. [94% decrease in peak P<0.0001]

Figure 34:
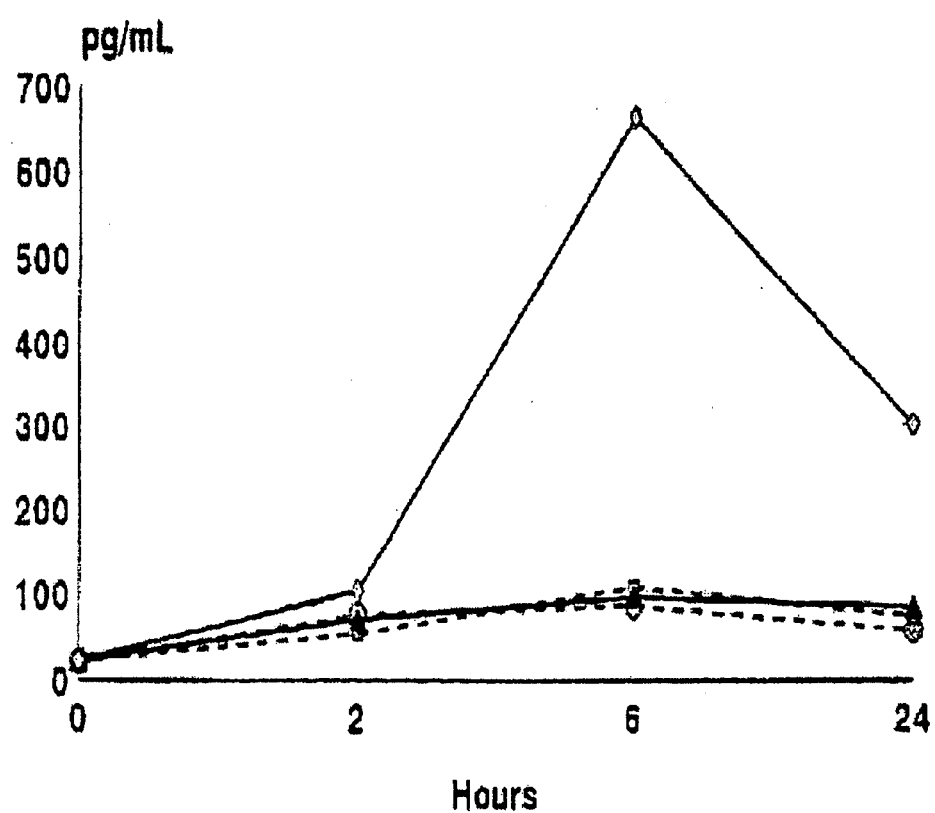

FIG. 34 is a graph of IL6 concentration following the administration of OKT3 and with microencapsulated TNFa, IL1$\beta$, or IL1+TNF neutralizing antibodies. Key: Diamond=OKT3 1 mcg/ml; triangle=TNF neutralizing antibody; square=IL1 neutralizing antibody; circle=TNF plus IL1 neutralizing antibody. [88% decrease in peak P<0.0001]

FIG. 35 is a table of the percent conjugation of MTX to PLGA with different ratios of carbodiimid to PLGA (Carbodiimide to TLGA ratio: 1:1, 2:1, 4:1, 8:1 and 12:1).

FIG. 36 is a table of the percent MTX remaining in a microcapsule after incubation with rat plasma, liver homogenate and phosphate buffer saline (pH 7.4). Values are represented as mean±standard deviation (N=4).

Figure 37:
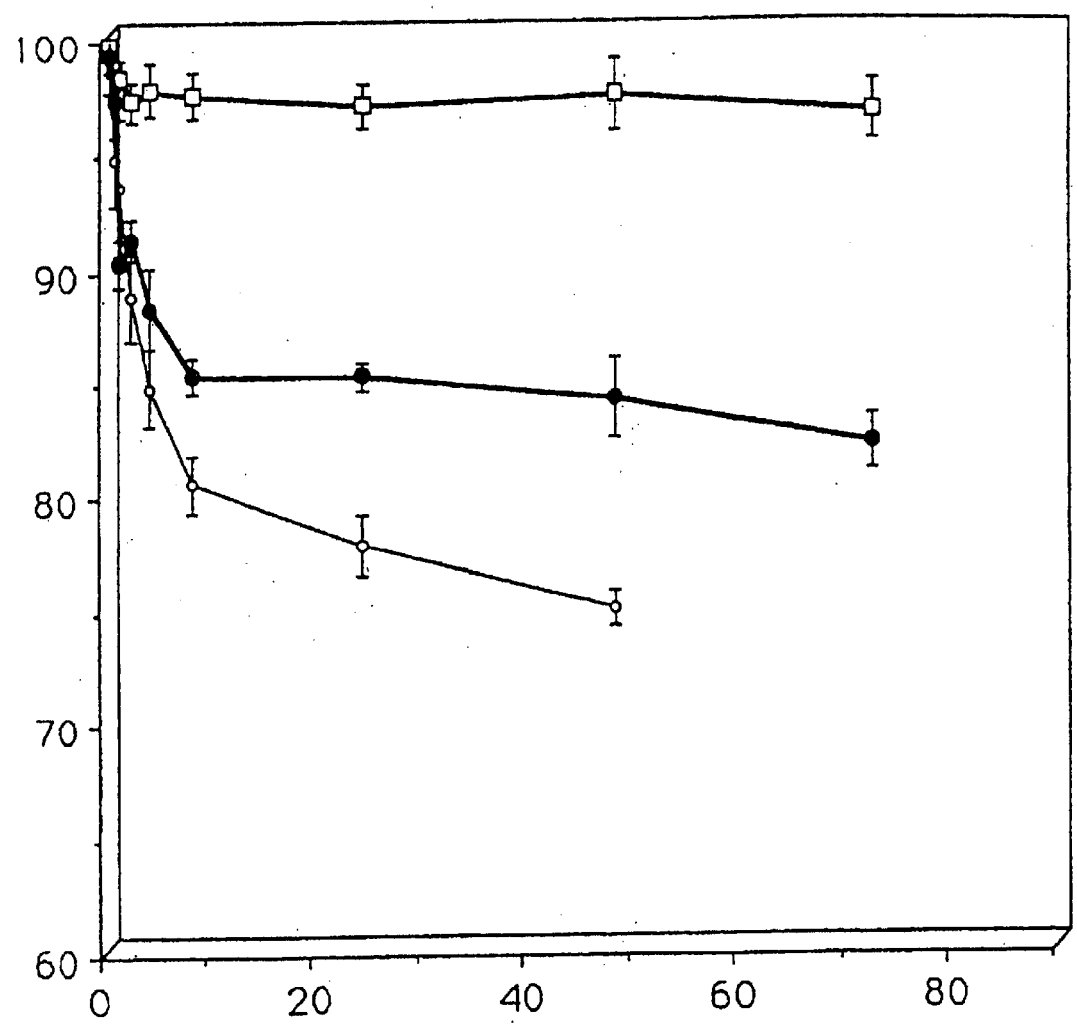

FIG. 37 is a graph of MTX release from microcapsules in presence of rat liver homogenate, rat plasma and phosphate buffer Data represent means±standard deviation (N=4). Key: Open circle=rat liver homogenate; black circle=rat plasma; open square=PBS (pH 7.4).

Figure 38:
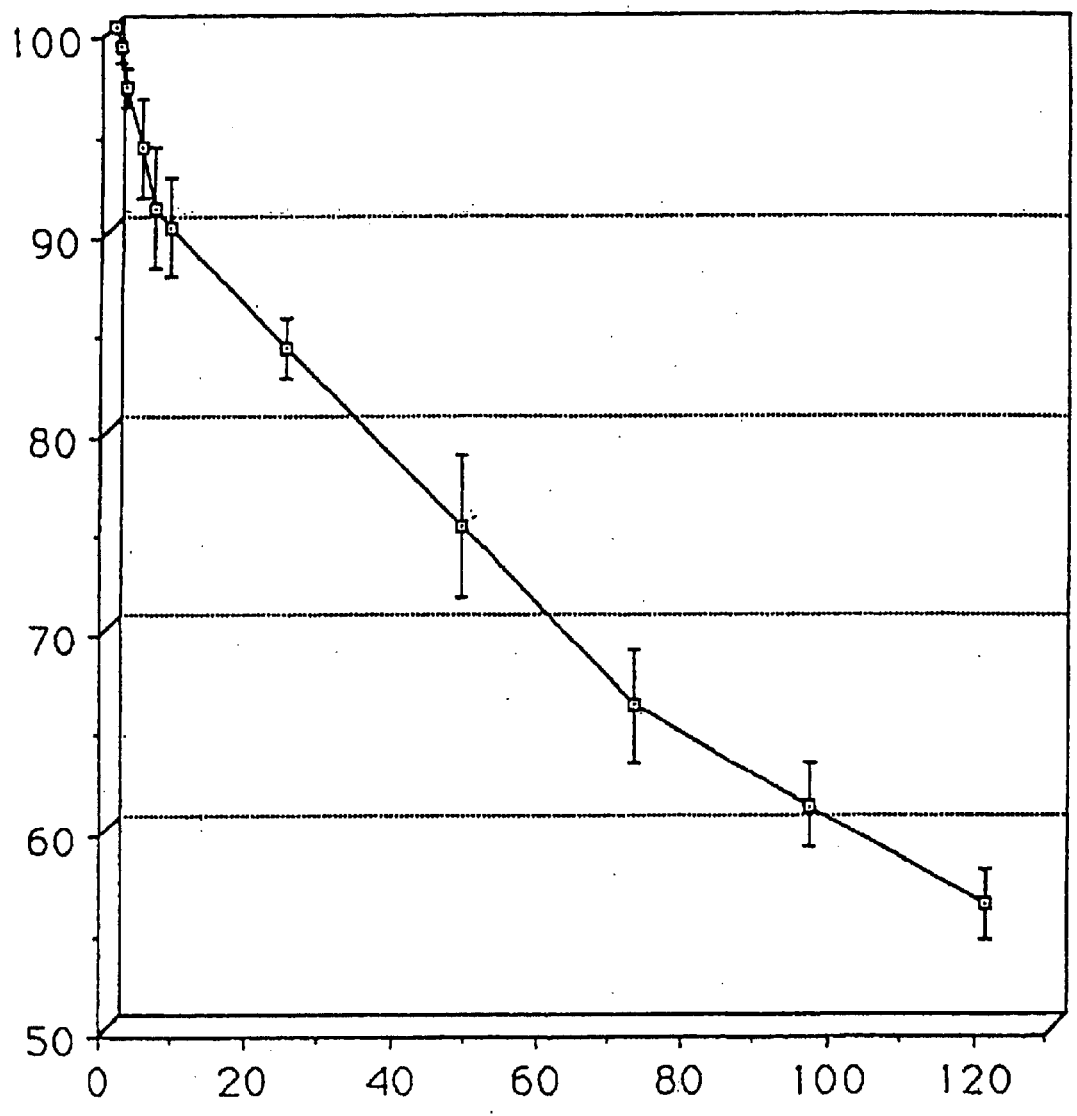

FIG. 38 is a graph of stability of MCSF microcapsules in PBS. Data presented as percent of M-CSF remaining in the microspheres (N=4).

Figure 39:
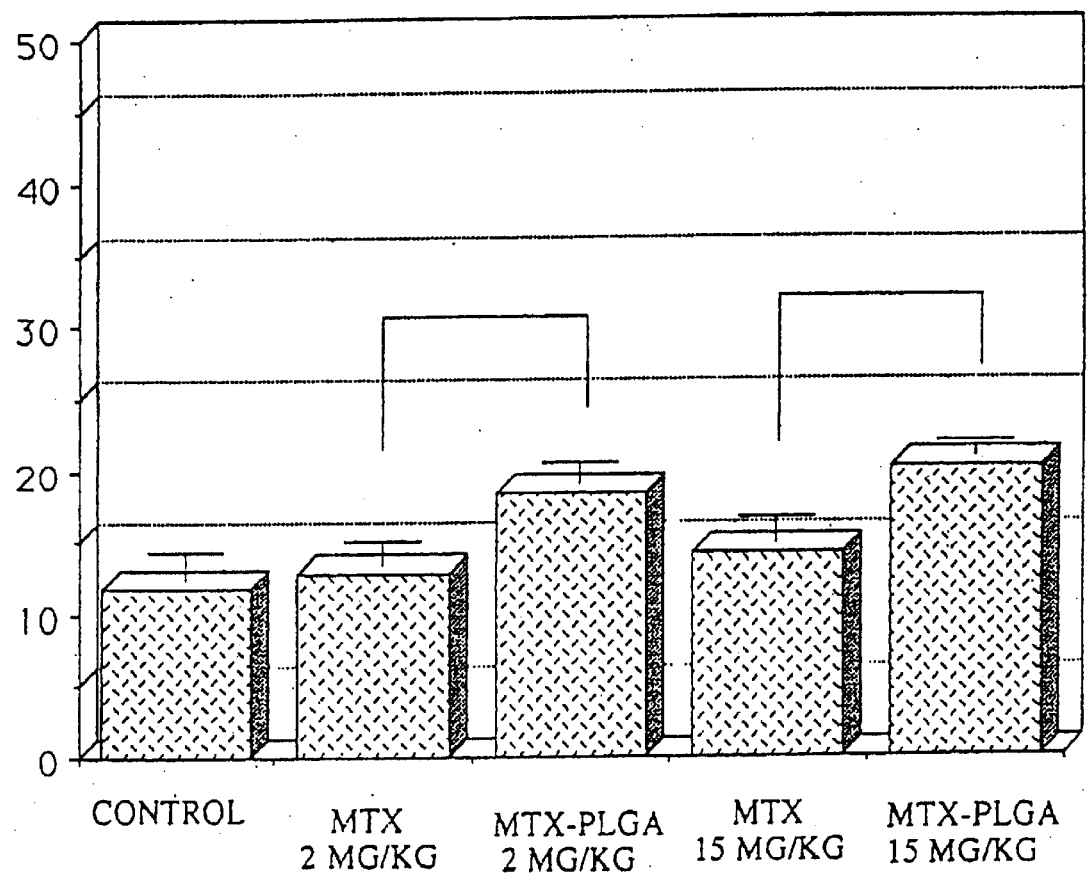

FIG. 39 is a graph of the effect of methotrexate solution versus methotrexate microspheres (s.c. every 3 days) on survival of animals with malignant melanoma. Data represented as mean days survived ( standard deviation, N=6). (Statistical significance p<0.05, ANOVA with multiple comparison test Tukey).

Figure 40:
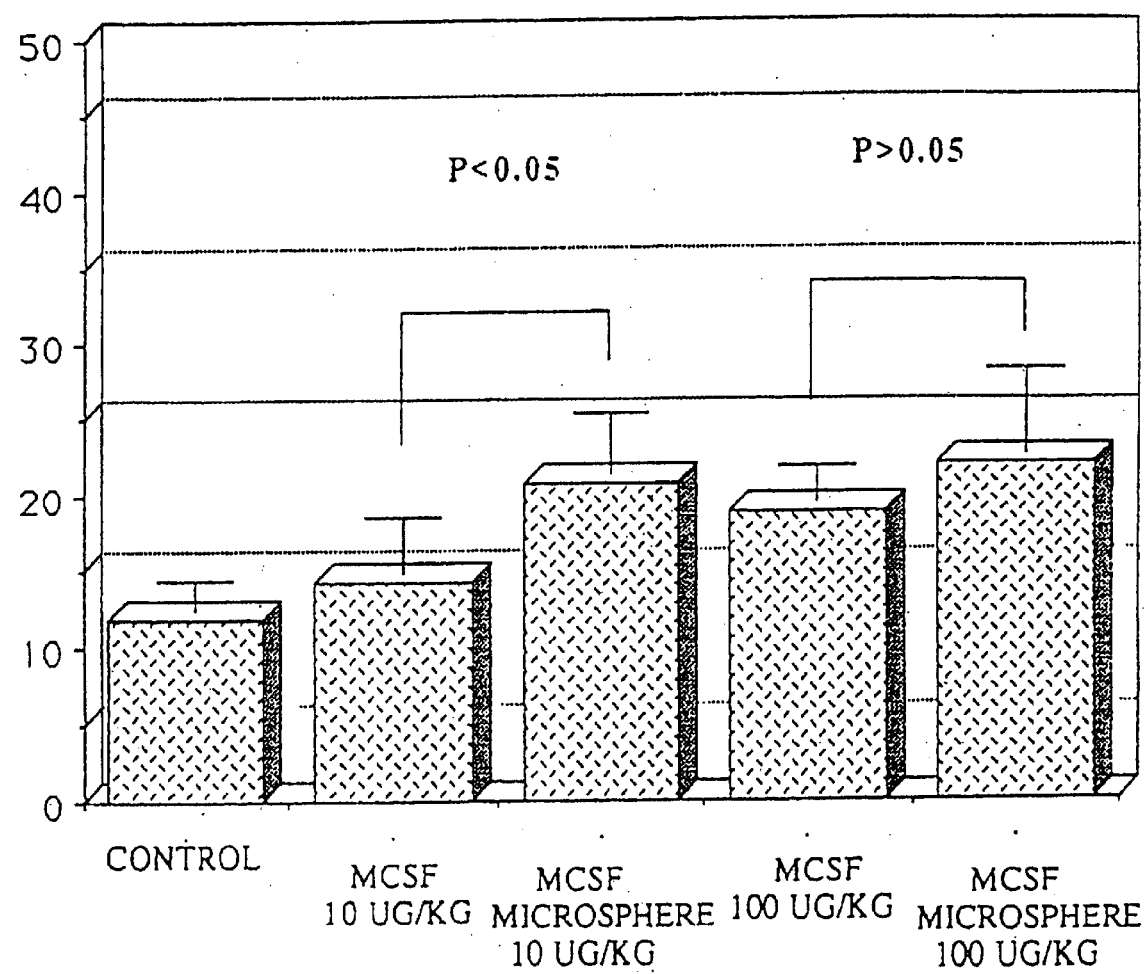

FIG. 40 is a graph of the effect rhM-CSF solution versus rhM-CSF microspheres (i.p. daily) on survival of animals with malignant melanoma. Data represented as mean days survived (±standard deviation, N=6). (Statistical significance p<0.05, ANOVA with multiple comparison test Tukey).

Figure 41:
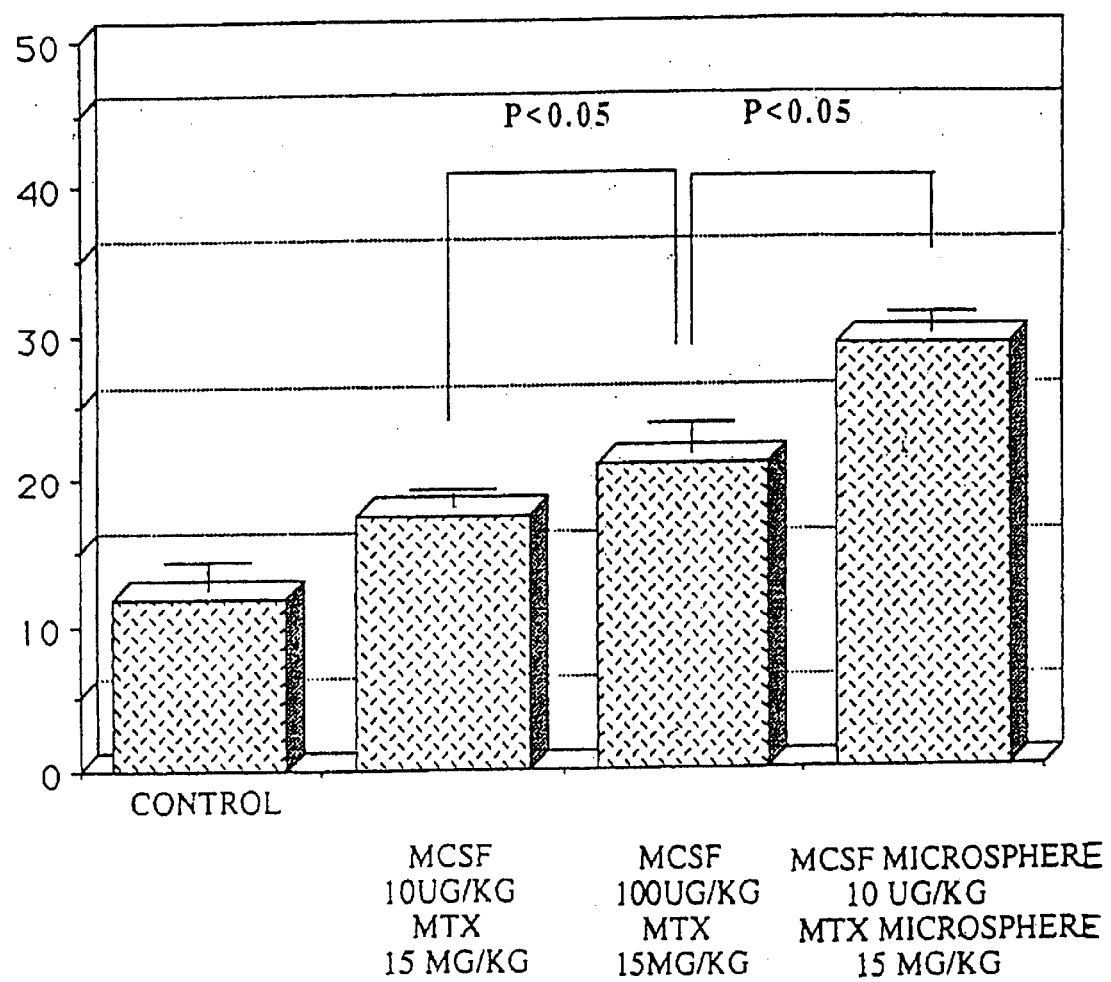

FIG. 41 is a graph of the combination therapy of rhM-CSF (i.p. daily) and methotrexate (s.c. daily) in the treatment of malignant melanoma. Data represented as mean days survived (±standard deviation, N=6). (Statistical significance p<0.05, ANOVA with multiple comparison test Tukey).

FIG. 42 is a table of IL1$\beta$ concentrations (pg/mL) in mice during treatment of malignant melanoma (N=6). Key: Q3 days=every 3 days injection; MTX-PLGA=methotrexate microspheres; MCSF Albumin=M-CSF microspheres; *=significantly different from the control p<0.05; +=significantly different from each other p<0.05.

FIG. 43 is a table of IL1β concentration in mice during treatment of malignant melanoma (N=6). Key: MTX-PLGA=methotrexate microspheres; MCSF Albumin=M-CSF microspheres;=significantly different from the control p<0.05; +=significantly different from each other p<0.05.

FIG. 44 is a table of TNFa concentration in mice during treatment of malignant melanoma (N=6). Key: Q3 days= every 3 days injection; MTX-PLGA=methotrexate microspheres; MCSF Albumin=M-CSF microspheres; *=significantly different from the control p<0.05; +=significantly different from each other p<0.05.

FIG. 45 is a table of TNFa concentration in mice during treatment of malignant melanoma (N=6). Key: Q3 days= every 3 days injection; MTX-PLGA=methotrexate microspheres; MCSF Albumin=M-CSF microspheres; *=significantly different from the control p<0.05; +=significantly different from each other p<0.05.

DESCRIPTION OF THE PREFERRED EMBODIMENTS

The cytokines and molecules against which neutralizing antibodies can be prepared include, but are not limited to, IL-1a, IL-1β, IL-2, IL-6, IL-8, TNFa, macrophage colony stimulating factor (MCSF), interferons, colony stimulating factor (CSF) and the like. For the purposes of the present invention "biological" is defined to mean any medically useful composition derived from a biological source and/or a synthetic pharmacological equivalent thereof. The term drug incorporates chemical and biological compounds, mixtures and materials useful in modulating, modifying or acting on a body, and are derivable from natural or artificial sources. A large number of water soluble and water insoluble drugs and other biologicals can be encapsulated and are contemplated by the present invention. An example of a typical drug is cyclosporin, which is discussed in detail hereinbelow.

Preparation of neutralizing monoclonal/polyclonal antibodies is well known in the art and need not be repeated here. The discussion of monoclonal antibodies is intended to include polyclonal antibodies and mixtures of each or both, hereinafter referred to as neutralizing antibodies (NA). The types of antibodies usable are preferably human, which present no immune cross-reactivity with antibodies in the human body. However, it is also possible to practice the present invention with other species of antibodies, such as those derived from murine, bovine, porcine, or other sources, or "humanized" animal antibodies.

It is possible that other cells, such as lymphocytes and leukocytes or dendritic cells can and will absorb the microspheres. Absorption of the microspheres may result in the passage of the encapsulated drugs across the blood brain barrier into the brain. Such a method may facilitate the transport of drugs to the central nervous system, providing treatment of brain-related diseases, including dementia and AIDS. Currently available delivery methods are normally unable to cross the barrier.

Materials that are biodegradable and nonantigenic can be used as the encapsulating material. In a preferred embodiment albumin is used. Albumin is a protein widely distributed throughout the tissues and fluids of plants and animals, such as in human serum. Albumin is used to encapsulate water soluble drugs. PLGA is used to encapsulate water insoluble drugs. Globulin can be used to encapsulate water soluble drugs. Natural or synthetic polymers can be used with the present invention, including thermoplastic polymers. A number of available crosslinking agents can be used.

In a preferred embodiment glutaraldehyde is used to crosslink the albumin after it has formed liquid bubbles around the antibody or drug of the desired size. The concentration of crosslinking agent affects the time the macrophage takes to digest the capsule material and release the drug. In this manner, the composition of the present invention can be designed for shorter or longer digestion. Additionally, the pharmaceutically delivered material may contain microspheres of encapsulated drug whereby the microspheres have different concentrations of crosslinking agent used, thereby creating a prolonged continuous release of the drug.

The storage lifetime of dried or lyophilized microspheres is exceptionally long. Samples have been kept for several years that have maintained their activity.

Any of several known pharmaceutical carriers can be used in the preparation of an injectable or otherwise administrable preparation, including phosphate buffered saline, saline, ethanol, propylene glycol and the like.

An advantage of the present invention is that a very low dose of NA is needed to produce cytokine inhibition. Additionally, using compositions encapsulated by albumin, NA are delivered to the target organ directly without systemic blood concentrations. Local activity is anticipated even when blood flow to the site of infection is poor. A sustained release of NA is produced within the macrophage as the microencapsulation is dissociated. A direct inhibitory effect of the NA on cytokine release from the macrophage is produced, rather than relying on inhibition of cytokine activity in the circulatory system. Intracellular release of NA may inhibit cytokine synthesis by macrophages. It is also possible that multiple NA may be encapsulated in a single microsphere to produce synergistic effects. Furthermore, systemic toxicity of NA is reduced. It should be observed in the examples below that inhibition of cytokine activity using the present invention is usually partial, not total, thereby allowing the body to fight infection.

The invention will be further described in connection with the following examples, which are set forth for purposes of illustration only. Parts and percentages appearing in such examples are by weight unless otherwise stipulated.

EXAMPLES

Example 1

A) Introduction

The cytokines tumor necrosis factor-a (TNFa) and interleukin-1β (IL-1β) have been implicated as immune modulators in a variety of acute and chronic diseases including pyrogenic reactions, septic shock, and human immunodeficiency virus wasting syndrome. A variety of models including human subjects, baboons, monocyte cell cultures, and whole blood have been used to study the release of these cytokines during experimental endotoxemia or bacteremia. Recently, clinical studies have demonstrated improvement in survival from a lethal endotoxin challenge in animals pre-treated with monoclonal antibodies (MoAb) to interleukin 1 receptor antagonist and TNFa. However, due to the high rate of clearance of the MoAbs, frequent doses of anti-cytokine MoAb are necessary to reduce mortality in endotoxin shock. In addition, no data exist to indicate that targeting systems for neutralizing antibodies would be effective in vivo or what type of matrices might be used to encapsulate water soluble compounds.

PREPARATION OF ANTIBODIES ENCAPSULATED BY ALBUMIN 1) 10 mg human albumin was dissolved in 1 cc pyrogen free water or phosphate buffered saline.

2) The antibody was separately solubilized in phosphate buffered saline (1 mg/cc).
3) The above two solutions were mixed together for approximately 30 minutes.
4) The resulting mixture of albumin and antibody was cooled to 5° C.
5) 10 cc of olive oil was taken in a 50 cc beaker and cooled to 5° C. and maintained at that temperature in an ice bath.
6) The mixture of albumin and antibody was added to the oil and emulsified with the aid of a Branson Sonifier at medium setting for 20 minutes.
7) The emulsion containing the microencapsulated albumin-antibody microspheres were evaluated for size with the use of a light microscope until the microsphere size were less than 1 micron in diameter.
8) The microspheres were crosslinked with 0.5 cc of a 25% solution of glutaraldehyde for 1 hour with constant stirring using a tissue homogenizer at high setting while maintaining the temperature at approximately 5° C. with the aid of an ice bath.
9) The microspheres were washed with three 20 cc washes of methanol and finally sized while being suspended in the final methanol wash, with the aid of sequential HPLC filters (50, 20, 10, 5 and 1 micron size).
10) The microspheres were dried in a vacuum desiccator for 5 hours or freeze dried and stored in a refrigerator until used.

In all cases the microspheres were suspended in pyrogen-free water before use.

Example 2

A) Introduction

One of the principal purposes of using microencapsulated cyclosporin (CsA) is to improve the existing treatment of rheumatoid arthritis by using CsA containing microspheres administered intraperitoneally. Since it is known that macrophages engulf foreign particles it is possible that they may re-localize at points of chronic inflammation and allow the CsA released from the biodegrading microspheres to inhibit T lymphocyte function thereby abolishing the inflammatory response in rheumatoid arthritis. In order to study the effects of cyclosporin loaded microspheres on macrophage disposition obtained from normal and arthritic rats, several types of microspheres were formulated and various in-vitro studies were carried out.

1. FORMULATION OF CYCLOSPORIN CONTAINING MICROSPHERES

A) "Cold" PLGA-CsA Microspheres 90 mg of PLGA 50:50 and 10 mg of CsA were dissolved in 10 ml of methylene chloride. The solution was emulsified into 100 ml of distilled water containing 2% w/v polyvinyl alcohol and 2% v/v Tween 80 using a biohomogenizer for 30 minutes. The contents were further emulsified using a Branson Sonifier probe (at a power level of 60) for 15 minutes to achieve an average emulsion droplet size of less than 2 microns. This process was continuously monitored by sampling the emulsion every 5 minutes and observing the emulsion under a light microscope. The emulsion was allowed to gradually warm up past this time by sonication at a power level of 40 for 30 minutes. This process was continuously monitored by sampling and observing the emulsion under a light microscope. The emulsion was allowed to gradually warm up past this time by sonication at a power level of 40 for 30 minutes. Methylene chloride was removed under reduced pressure. The formed microspheres were recovered by centrifugation at 6000 rpm for 20 minutes rinsed thrice with 100 ml portions of fresh distilled water.

PVA and Tween 80 were removed by dialyzing the microspheres in distilled water for 24 hours. Microspheres were placed in a desiccator and stored at −30° C. till used. Spherical CsA and aminopolystyrene containing microspheres were successfully formulated in the 0.22 μm–0.8 μm range.

B) PLGA-3H-CsA Microspheres

Formulation procedures were identical to the above procedure except that 3H CsA (50 microliters, 1 microcurie/microliter) was added to the "cold" CsA solution in methylene chloride.

2. FORMULATION OF NON-CYCLOSPORIN CONTAINING MICROSPHERES

A) PLGA-Aminopolystyrene Microspheres 75 mg of PLGA 50:50 and 25 mg aminopolystyrene were dissolved in 10 ml of 70:30 methylene chloride and 1-methyl 2-pyrrolidine. The solution was dispersed into 100 ml of distilled water containing 5% v/v Tween 80 and 2% v/v polyvinyl alcohol using a propeller stirrer for 5 minutes at 800 rpm. The contents were further emulsified using a Branson Sonifier probe (at a power level of 60) for 15 minutes to achieve an average emulsion droplet size of less than 2 microns. This process was continuously monitored by sampling the emulsion every 5 minutes and observing the emulsion under a light microscope. The emulsion was allowed to gradually warm up past this time by sonication at a power level of 40 for 30 minutes. The formed microcapsules were centrifuged out at 6000 rpm for 20 minutes rinsed thrice with 100 ml portions of fresh distilled water placed in a desiccator and stored at −30° C. till used.

B) Formulation of Blank Microspheres

Microspheres of PLGA alone were prepared using the same procedure as above. 10 ml of methylene chloride was used as the internal phase.

3. SIZING OF MICROSPHERES

Microspheres were sequentially filtered through 10 μm, 2 μm, 0.8 μm and 0.22 μm nylon HPLC filters to obtain a working size range for the in-vitro and in-vivo studies. Particles between 0.22 μm and 0.8 μm were used for all studies.

4. RADIOLABELING OF PLGA-AMINOPOLYSTYRENE MICROSPHERES

A bifunctional chelate-2, 3, 5, 6 tetra fluorophenol mercaptoacetyl diglycine-gamma butyrate (MAG2-GABA-TFP, 0.3 mg; Neorx, Corpn.) was dissolved in 0.9 ml isopropyl alcohol. 0.6 ml of this solution was acidified by addition of 0.16 ml of glacial acetic acid-0.2 N HCl (2:14). The acidified ligand (0.5 ml) was added to a tube containing premixed stannous gluconate complex (Sodium gluconate 50 mg, Stannous gluconate dihydrate 1.2 mg per ml) and Technetium 99 metastable (99mTc) (about 100 mCi/ml). The contents were incubated at 75° C. for 15 minutes and then neutralized with 0.5 ml of bicarbonate buffer. A known amount of PLGA-aminopolystyrene microspheres in saline suspension was added to the activated ligand and allowed to incubate for 30 minutes. The reaction contents were centrifuged and washed twice with pH 7 buffer phosphate buffered saline in order to remove unreacted free 99mTc complex. A dose calibrated aliquot of the microsphere suspension was used for various studies.

Figure 1:
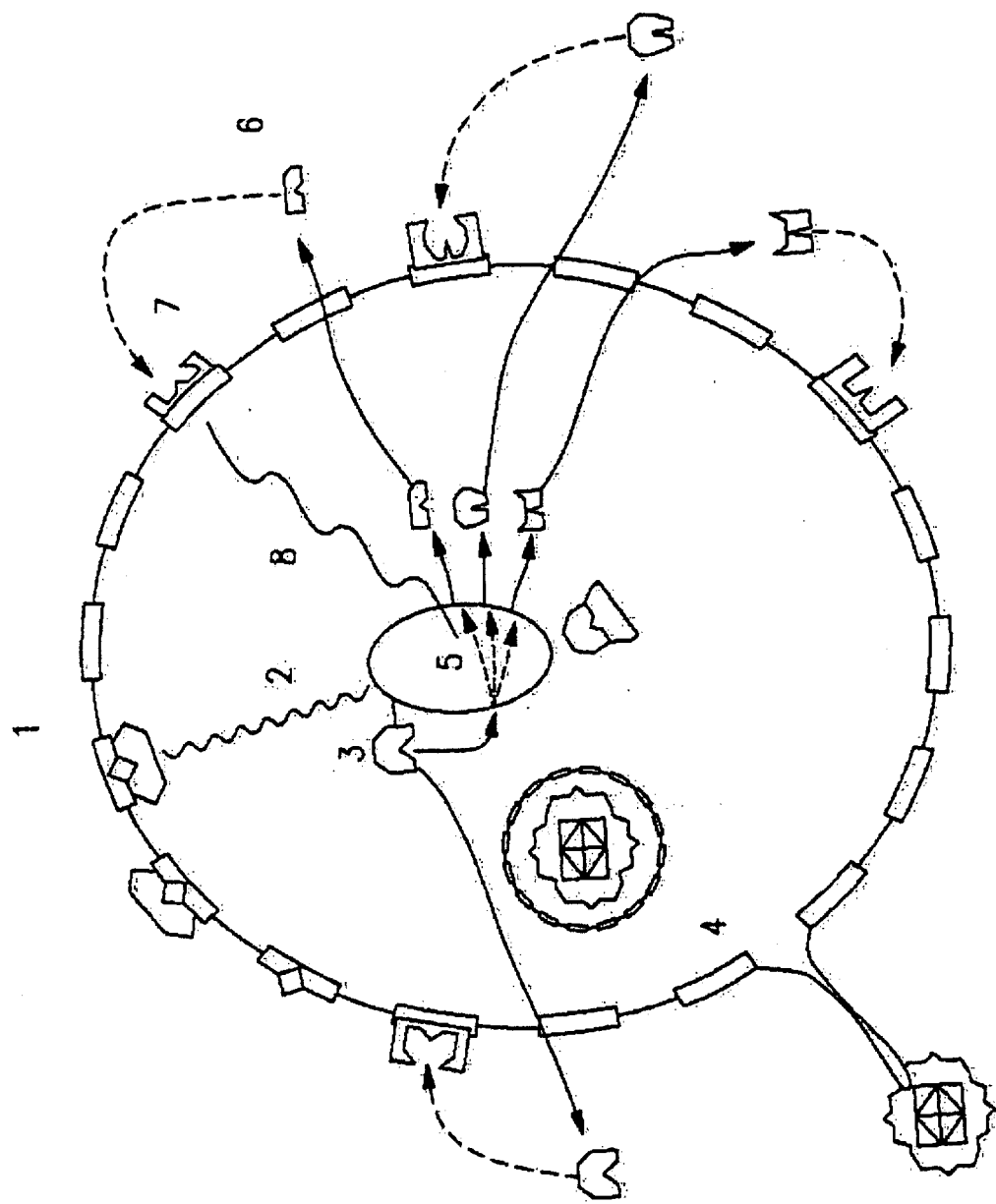
Figure 2:
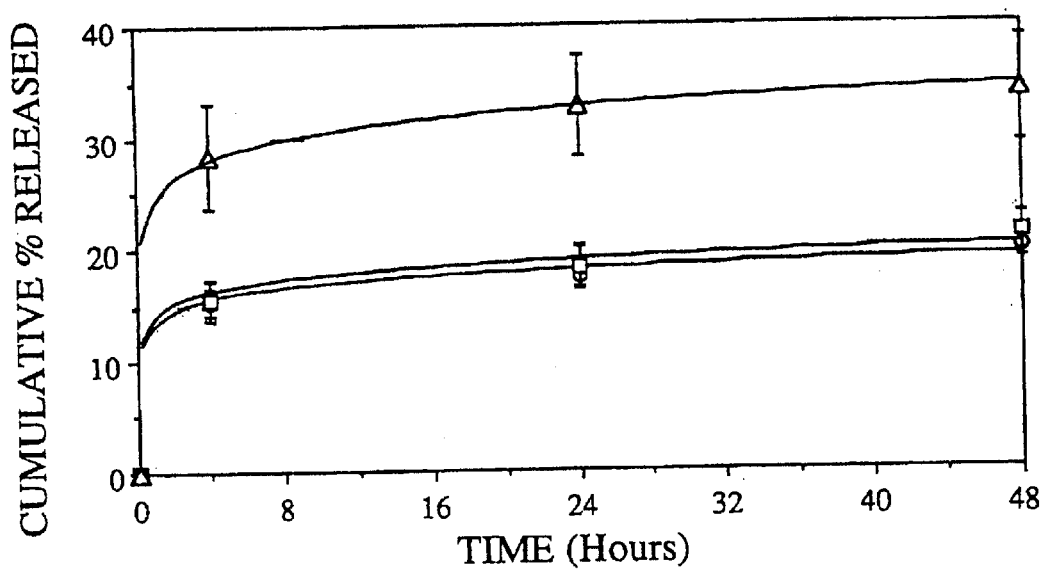

At least 50% radiolabeling efficiency was achieved using the MAG2-GABA TFP radiolabel technique in all studies. The aminopolystyrene was incorporated into the microsphere in order to provide an amine (NH$_2$) functional group for radioligand attachment. An amide linkage is formed between this group and the radioligand. A graph of cumulative % radiolabel released versus time for 99mTc radiolabeled microspheres in PBS, culture medium and rat plasma is shown in FIG. 2. The curve fitted equations predict that over 90% of extractable radiolabel is released into the supernate within 1 hour. From the above data it was decided to allow all 99mTc radiolabeled microspheres to incubate in phosphate buffered saline for 1 hour in order to leach out unbound radiolabel before use in all further studies requiring 99mTc radiolabel.

5. IN-VITRO DISSOLUTION KINETICS OF CYCLOSPORIN FROM PLGA-CsA MICROSPHERES 4.95 mg of CsA containing PLGA microspheres of 0.22 µm–0.8 µm diameter was placed in a dialysis bag (MW= 14,000 cut off) before being incorporated within a USP basket assembly and stirred at 100 rpm in pH=7.3 phosphate buffer for 48 hours. 2 ml aliquots of the dissolution medium were sampled at 0.5, 1, 2, 4, 8, 24 and 48 hour intervals. CsA concentrations were measured using an RIA kit (Incstar, Inc.). A cumulative percent CsA release versus time plot was constructed FIG. 3. Microspheres were found to contain 9.38% w/w of "cold" CsA. The target encapsulation efficiency was 10% w/w. This corresponds to an overall encapsulation efficiency of over 99%. The lipophilic nature of CsA would help account for high entrapment efficiency.

Dissolution rates of CsA from the microspheres were extremely slow in the 48 hour study (FIG. 3). Only 0.002% of the available CsA in the microspheres leached out into the dissolution medium at 48 hours. A small burst effect is observed up to 8 hours. This proved that CsA is effectively entrapped within the PLGA matrix.

6. MICROSPHERE UPTAKE BY MACROPHAGES

A) Cell Isolation Procedures

Peritoneal exudate cells were isolated from unstimulated normal and arthritic rats. The cells were isolated using 50 ml of glucose nutritive medium (GKN) composed of HBSS supplemented with 0.2% glucose, centrifuged at 400 g, resuspended briefly in 1 ml of distilled water in order to lyse red blood cells and restored to isotonicity using 1 ml of 1.8% w/v NaCl. The cells were then plated in 100 ml culture flasks containing 25 ml of culture medium -RPMI 1640 (Gibco Laboratories) supplemented with 10% fetal calf serum (Gibco Laboratories) for 1.5 hours. Culture medium containing non adherent cells was aspirated out, and the flask rinsed twice with GKN. The adherent cells were gently scraped off the flask using a rubber policeman, counted in a hemocytometer and tested for viability using trypan blue. The macrophages were then diluted in culture medium to obtain a final dilution of 0.5×10$^7$ cells in 2 ml. Two ml of cell suspension were plated in 25 ml culture flasks in a CO$_2$ incubator (37° C., 5% CO$_2$) for 1.5 hours before use.

B) Study Protocol

Microsphere uptake studies were carried out over 1 hour. Six flasks were used for each time point. A stock suspension of 99mTc radiolabeled microspheres in RPMI 1640 supplemented with 10% fetal calf serum (FCS) was prepared so that 1 ml of stock suspension contained 5×10$^7$ microspheres. Serial dilutions of the stock solution were carried out to obtain microsphere suspensions of 2.5×10$^7$ microspheres/ml and 0.5×10$^7$ microspheres/ml. 2 ml of each microsphere suspension were placed in sets of twenty four flasks each, containing plated macrophages (1×10$^7$ cells). At 15 min, 30 min, 45 min and 1 hour culture medium containing nonphagocytized microspheres was withdrawn from six flasks, the flasks rinsed twice with 1 ml portions of fresh culture medium and the culture medium along with the rinses placed in a tube. Adhered cells were dissolved using 2 ml of 2% w/v sodium dodecyl sulfate (SDS). The flasks were rinsed twice with 1 ml portions of SDS and the dissolved cells along with the washes were measured for 99mTc radiolabel activity using a gamma counter (Tracor Analytic).

Figure 4:
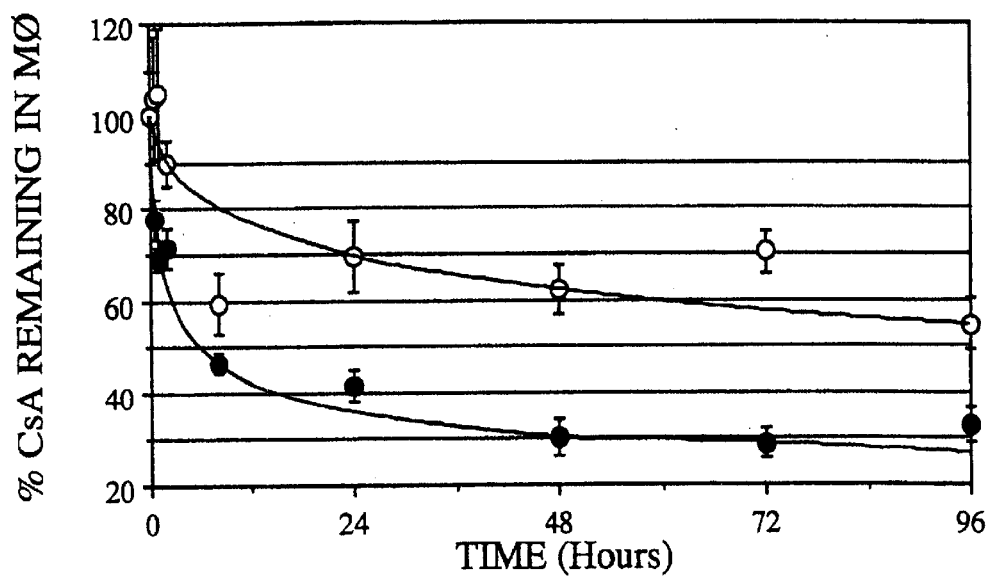

Percent uptake (percent activity of the cell fraction) was expressed as a percent of the total activity in each flask according to the formula:

% Uptake=Activity of Cell fraction×100 Activity of Cell Fracion+ Activity of Culture Medium FIG. 4 describes 99mTc-PLGA microsphere uptake profiles of normal and arthritic macrophages in-vitro. Maximal uptake at the end of 1 hour was exhibited by normal macrophages. Normal macrophages exhibited greater than 90% viability at all dose levels at the end of 1 hour. No significant dose related differences were observed in the case of normal macrophages (ANOVA, Repeated measures, p<0.05) but the highest dose ratio (10:1) in the case of the arthritics exhibited significant differences with time when compared to the other doses (ANOVA, Repeated measures, p<0.05). Uptake profiles were found to be significantly different normal and arthritic macrophages at each dose ratio (ANOVA Repeated measures, p<0.05). In the case of the arthritic macrophages the highest uptake was observed at 15 minutes (27% dose, 10:1 microsphere to macrophage ratio) and was found to be significantly different from the other dose ratios at that time but also through the rest of the study. It may be that the high microsphere loading of arthritic macrophages, due to their increased state of activation, contributed to cell cytotoxicity.

7. RELEASE PROFILES FROM MACROPHAGES CONTAINING CsA MICROSPHERES IN-VITRO

Peritoneal exudate cells were obtained from normal and arthritic rats after i.p. injection of 45 ml chilled Hanks' Balanced Salt Solution (HBSS). Contaminating red blood cells were lysed by pulsing with 1 ml of distilled water followed by 1 ml of 1.8% w/v NaCl solution. The cells were plated in culture flasks containing RPMI 1640 supplemented with 10% FCS for 2 hours before removal of non-adherent cells. After 3 rinses adherent cells were scraped off the flasks, counted and tested for viability using trypan blue. 1 ml aliquots of 5×10$^5$ macrophages in culture medium (RPMI 1640 supplemented with 10% fetal calf serum) were placed in 1.1 ml culture tubes (Skatron, Inc., Norway). 0.1 ml aliquots containing 5×10$^5$3H-CsA microspheres (0.22–0.8 micron diameter) were added to each tube. The tubes were lightly capped and placed in a CO$_2$ incubator (37° C., 95% humidity) for 1 hour in order to allow the macrophages to engulf the microspheres. CsA release studies were carried out at this point of time. At 0.5, 1.0, 2.0, 4, 8, 20, 24, 48, 72, and 96 hr, groups of 6 tubes were harvested using a cell harvester (Skatron Inc., Norway) equipped with 9 mm glass fiber filtermats that retain particles over 1 micron in size. The filter discs were transferred to scintillation tubes and allowed to dry overnight 1 ml of acetone was added to each tube to dissolve CsA and microspheres engulfed within cells. 200 microliters of SDS followed by 10 ml of scintillation cocktail (Beckman) was added to each tube. Counts (cpm) were obtained using a liquid scintillation counter (Beckman LS 2000) and interpreted as percent of the control (lymphocytes exposed to thymidine only) counts.

CsA levels within macrophages (normal and arthritic) decreased exponentially in the first 24 hours but were almost constant thereafter up to the end of the study period (96 hours). Normal macrophages retained a higher percentage of CsA either entrapped within microspheres or released within the cytoplasm of the macrophage in this time period as compared to arthritic macrophages. Higher levels (52% CsA dose) in normal macrophages compared to arthritic macrophages (32% CsA dose) may be explained on the basis of macrophage activation. Activated macrophages possess a more acidic environment which could lead to increased catalytic degradation of PLGA. Also since activated macrophages are more phagocytic in nature an increased amount of CsA released into the cell cytoplasm from the engulfed microspheres may be excreted extracellularly during the process of phagocytosis. The initial exponential decline is characteristic of drug diffusion; however, the drug levels do not fit the classical Higuchi plot equations for drug diffusion from an insoluble matrix nor do they fit a first order exponential equation. Therefore it must be assumed that some other process or combination of processes is in operation. A burst effect may be in operation in the first 24 hours. It must be noted that the drug content of CsA microspheres used in the present studies was relatively high (above 9% w/w) as compared to microspheres prepared by other researchers (maximum 7%). At this level of drug loading it has been documented that a substantial burst effect occurs and that the normal biphasic drug release pattern from the PLGA microsphere is disrupted leading to a merging of the release profiles contributed by diffusion and subsequent erosion.

8. IN-VITRO INHIBITION OF MIXED LYMPHOCYTE CULTURE PROLIFERATION BY MACROPHAGES CONTAINING MICROSPHERES

Macrophages were isolated from normal and arthritic male Sprague Dawley rats as previously described. Aliquots of $1\times10^5$ macrophages in 0.4 ml of culture medium were used in all experiments. Mixed lymphocyte bands from diluted peripheral blood (1:2 in isotonic saline) from separate normal and arthritic rats were obtained using a density gradient procedure (ficoll-24 parts, 9% w/v and hypaque-10 parts, 40% w/v). Contaminant RBC's were lysed by pulsing with hypotonic saline and the lymphocytes were counted and tested for viability using trypan blue. Aliquots of $1\times10^5$ lymphocytes in 0.4 ml of culture medium were used for all experiments.

Blank and CsA containing microspheres ($1\times10^5/0.1$ ml) and CsA solution (1.1387 micrograms/0.1 ml) were preincubated with macrophages for 1 hour in a $CO_2$ incubator prior to use. Lymphocyte suspensions (0.4 ml) were added to each group of 6 tubes. 3H-Thymidine (0.1 ml, 20 microcuries/ml) was added after 24 hours to all tubes. Thymidine incorporation into transformed lymphocytes was measured at 48 hours after addition to the tubes. Details of the protocol are listed in FIG. 5. Cells were recovered using a cell harvester and counts per minute of 3H-thymidine were obtained using a liquid scintillation counter. Percent inhibition of 3H-thymidine uptake was interpreted as the in-vitro % inhibition of lymphocyte activity by blank microspheres, CsA in solution or CsA within microspheres.

Figure 6A:
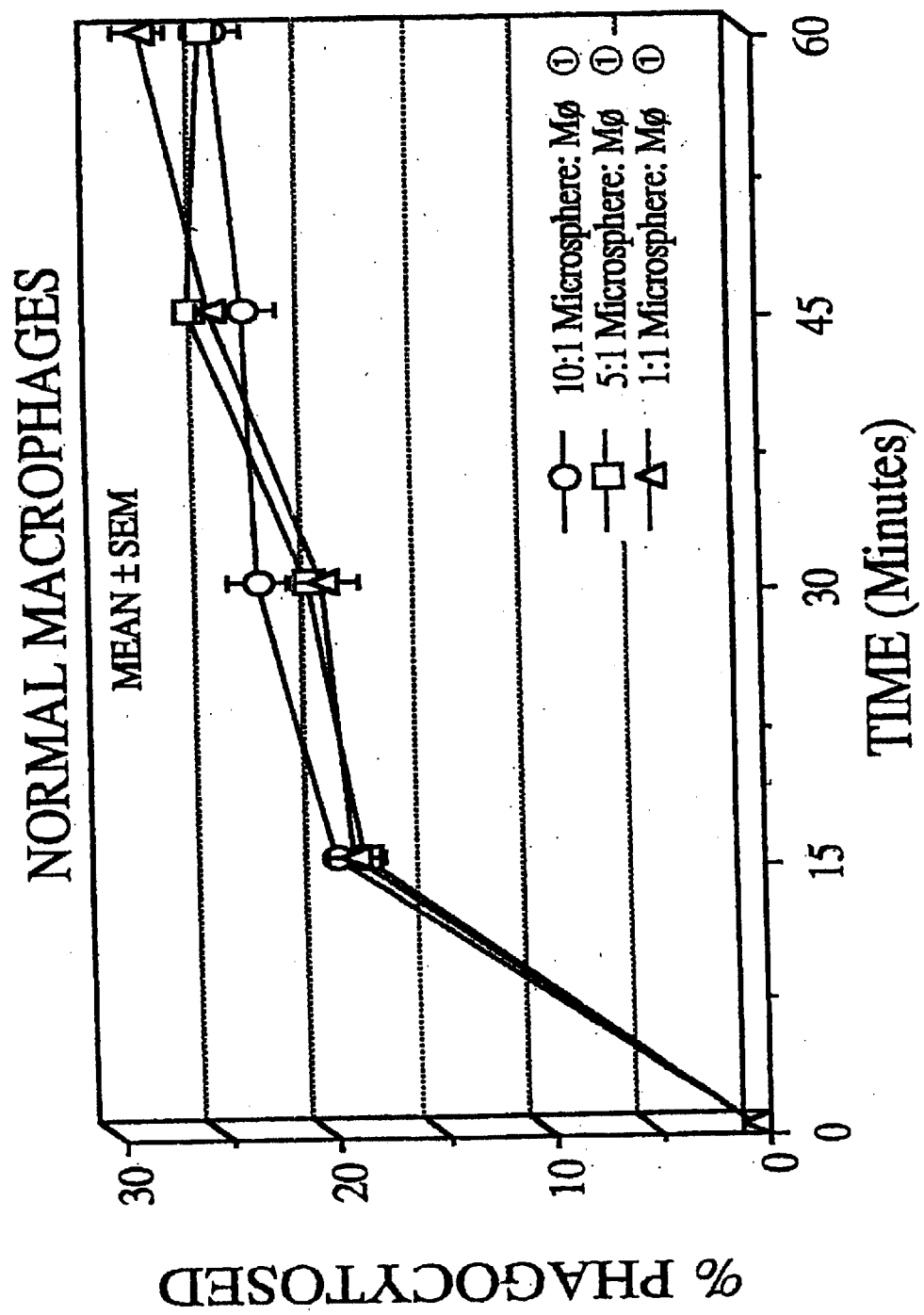
Figure 6B:
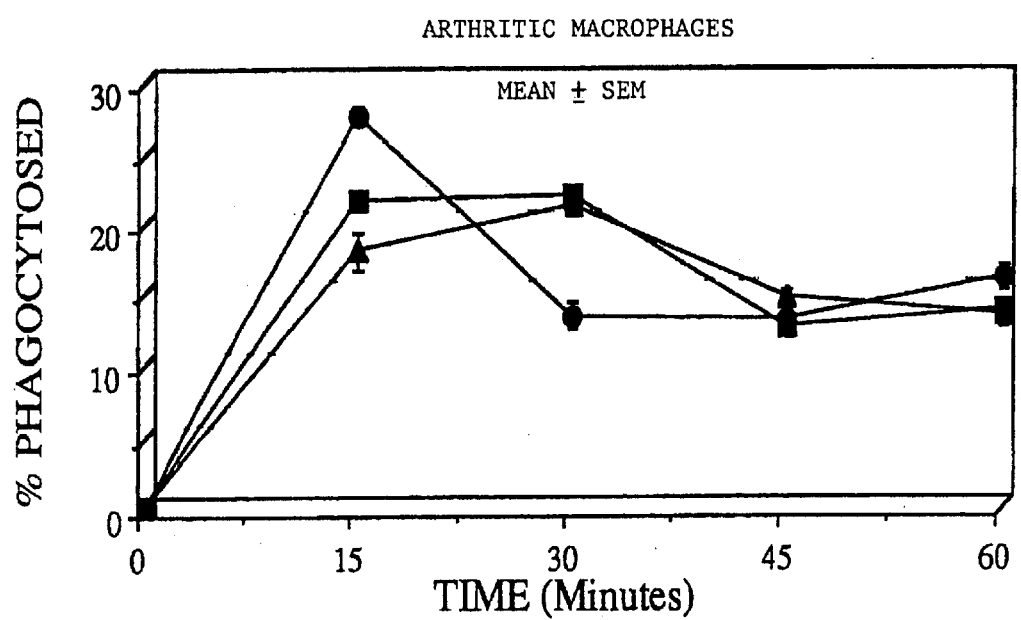
Figure 7A:
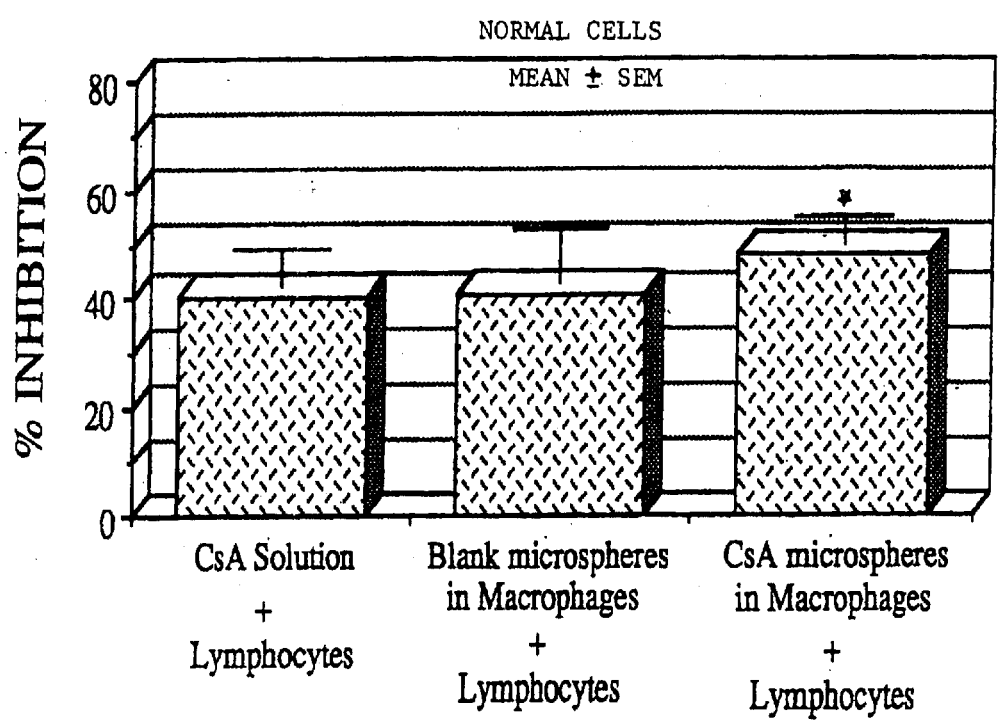
Figure 7B:
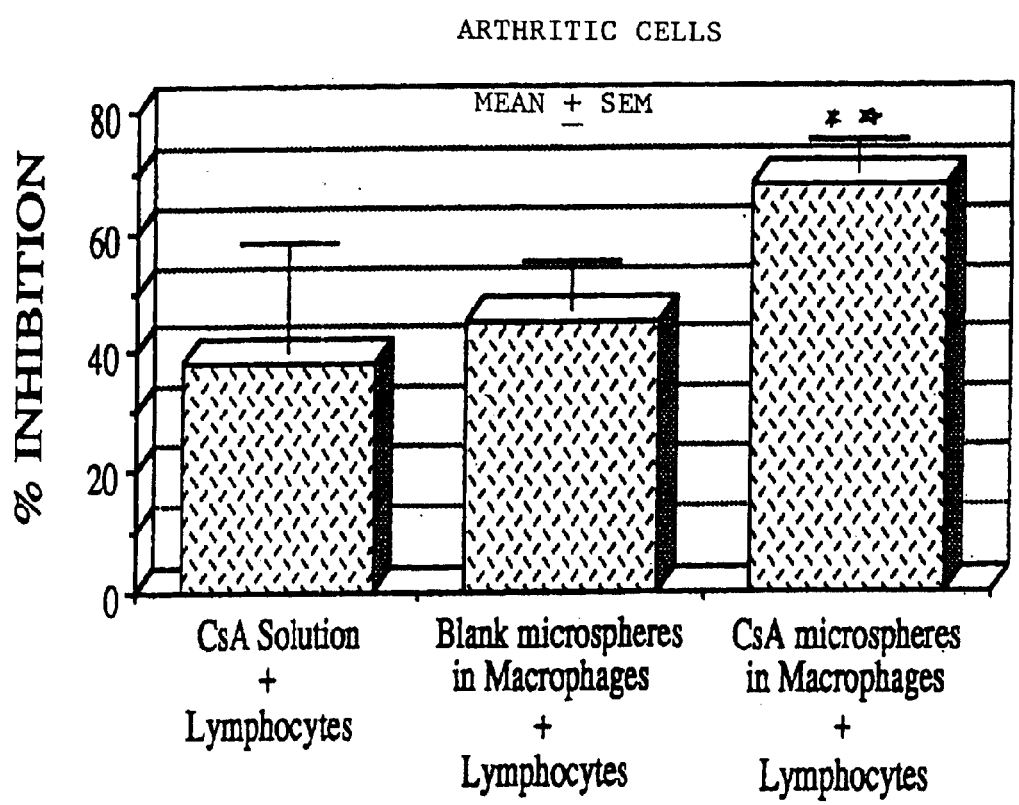

The effect of various pretreatments on transformation of normal and arthritic lymphocytes after addition of thymidine at 24 hours is shown in FIG. 6 and 7 included herein. In studies involving normal cells no significant differences in lymphocyte transformation were observed between the effect of CsA in solution or that of macrophages previously presented with CsA microspheres. However CsA microspheres within arthritic macrophages produced significantly increased inhibition ($p<0.05$) of lymphocyte transformation (68.17±11.2%) compared to the effect of CsA in solution (38±32.07%) or blank microspheres within macrophages (44.7±20.51%). Additionally this group was found to be significantly different from the corresponding group of normal cells (CsA microspheres in normal macrophages+ normal lymphocytes, 48.2±11.3%). The increased inhibition may stem in part from higher CsA levels associated with arthritic macrophages which may in turn be due to the higher activation levels of these macrophages.

9. IN-VIVO STUDIES: METHODS

A) Animals

Male Sprague Dawley rats (200–225 gms, 7 weeks old) were used in all experiments. They were housed in individual cages and allowed free access to food and water.

B) Induction of Arthritis

Rats were injected into the subplantar region of the right hindpaw with 4 mg Mycobacterium butyricum (Difco Laboratories) suspended in 0.1 ml of light mineral oil. The development of arthritis in both hindpaws was followed plethysmographically by mercury displacement on days 21, 28, 35, and 42 (Week 0, Week 1, Week 2, Week 3) post-adjuvant injection. Blood samples were drawn on the same days to measure whole blood CsA trough levels and obtain serum biochemistries.

C) Dosing Protocol

To determine the ability of CsA and CsA microspheres to inhibit the established disease, CsA microspheres (1 mg/kg and 2.5 mg/kg) and CsA in oil (1 mg/kg and 2.5 mg/kg, 6 rats) were administered intraperitoneally (i.p.) every 2 days to separate groups of rats commencing day 21 post-adjuvant injection. Additionally, a single CsA microsphere dose of 1 mg/kg i.p. was administered to a group of 6 rats.

Positive controls (rats with adjuvant arthritis) were administered blank PLGA microspheres (1 mg/kg and 2.5 mg/kg) suspended in saline. Negative controls (normal rats) also received blank PLGA microspheres (1 mg/kg and 2.5 mg/kg) suspended in saline.

D) Assay Procedures

Blood samples (1 ml) were obtained each week by tail snips in EDTA coated tubes. The samples were centrifuged at room temperature and 25 microliters of the plasma was assayed for CsA content using an RIA kit (Cyclo-trac, Incstar). Serum biochemical parameters were measured on a Kodak automated analyzer.

5. Calculations: Percent inhibition in arthritis was calculated using the formula below:

$$\% \text{ Inhibition} = \frac{(V - V_{Neg}) \times 100}{(V_{Pos} - V_{Neg})} - \text{Average \%inhib at Week 0}$$

where V=Paw volume of test rat

Vneg=Average paw volume of negative controls on same day

Vpos=Average paw volume of positive controls on same day

Average percent inhibition of arthritis and standard error was calculated for hindpaws of animals in each group. The %Inhibition vs Time (weeks) were constructed for the 5 dosing regimens (Microspheres: 1 & 2.5 mg/kg/2 days, 1 mg/kg once and CsA 1 and 2.5 mg/kg/2 days) for each hindpaw using the above formula.

E) Results

Percentage inhibition of arthritis in the left hindpaw was maximum at week 1 for the 2.5 mg/kg multiple dosing regimen (62%) whereas it was maximum at week 2 for the right hind paw (72%). Inhibition of arthritis with the 1 mg/kg multiple dosing regimen was lower in both paws (23% left, 23% right) and the 1 mg/kg dose given once (3% left and 12% right). In the latter cases peak inhibition occurred at week two for both hindpaws and tended to remain fairly constant through week 3 for the right hindpaw but declining inhibition was observed in the left paw data. During the study period (3 weeks) the group administered CsA 1 mg/kg i.p. did not show any improvement in arthritis. A one week lag period was required for any discernible improvement in arthritis in either hindpaw using a single dose of 1 mg/kg. Results for all microsphere dosing regimens were significantly different (p<0.05) from the corresponding CsA treated regimens.

Figure 8A:
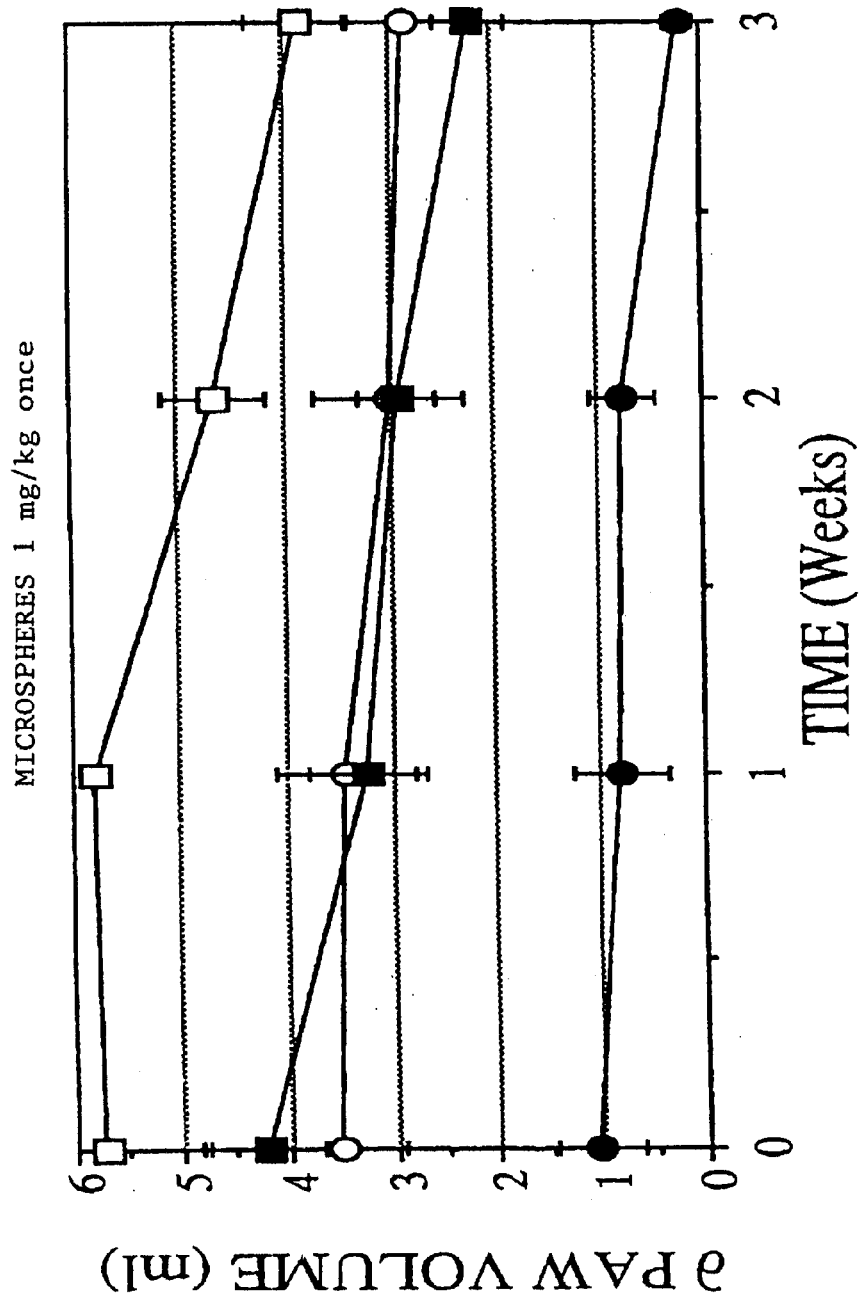
Figure 8B:
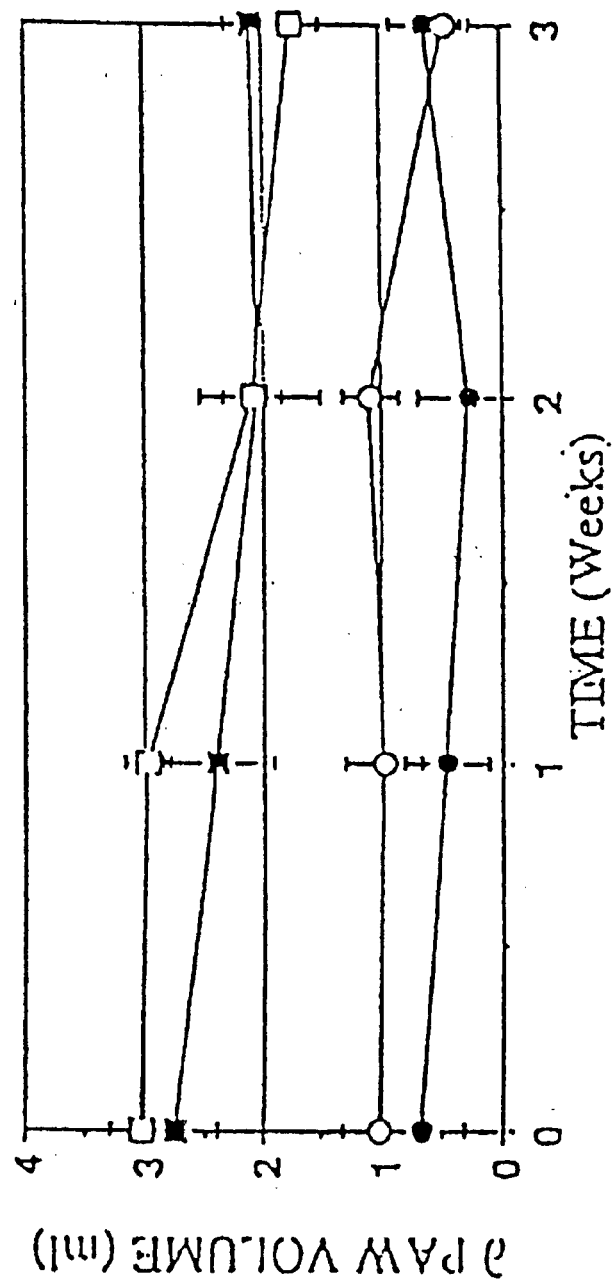

Plasma or serum CsA levels are presented FIGS. 8A and B. It may be noted that these levels were consistently below the minimum detectable limit (20 ng/ml) throughout the study.

Example 3

A) Introduction

Sepsis due to gram negative bacteria is a significant clinical problem despite the advent of antibiotics. Hallmark complications of septic shock include cardiovascular collapse, increased vascular permeability, pulmonary dysfunction, fever, and alterations in lipoprotein lipase activity characterized by a wasting syndrome. The exact molecular events leading to the progression of sepsis are not clearly understood, however, recent studies have observed that the host response to the invading pathogen contributes to the pathogenesis of sepsis. The cytokines tumor necrosis factor alpha (TNFa) and interleukin-1 beta (IL-1β) have been implicated as principle immune modulators released from activated macrophages during experimental endotoxin shock. The use of monoclonal antibodies (MoAb) against TNFa, given within minutes of an intravenous septic challenge, have been shown to be beneficial in reducing mortality of septic shock. However, intravenous MoAbs require frequent, high dosing to provide protection from bacterial sepsis. In addition, pre-treatment with the MoAbs may not be clinically appropriate since sepsis is not a predictable clinical event. In contrast, cytokine MoAbs have not been shown to be effective in models of sepsis other than intravenous bacteria administration. The effectiveness of TNFa MoAb in intravenous sepsis has been demonstrated, but the TNFa MoAb was unable to prevent lethality in a peritoneal sepsis model. Likewise, others have failed to prevent lethal sepsis with TNFa MoAb following cecal ligation and bowel perforation in mice.

1. IN VITRO MICROENCAPSULATED NEUTRALIZING ANTIBODIES FOR EXPERIMENTAL ENDOTOXEMIA/SEPTIC SHOCK

A) Preparation

Microencapsulated NA were made according to Example 1. The concentration of albumin and NA were varied depending upon the NA used.

B) Experimental Method 1. 100 ml of whole blood from humans were obtained.
2. The blood was divided into aliquots.
3. The following groups were used: Endotoxin-free water (EFW); Blank microsphere containing no drug (MC); MC (blank with 100 ng/ml *Escherichia Coli* (*E. coli*)); NA to TNFa, IL-1β, IL-6, and IL-8 and IL1-ra.
4. A) Stimulation with *E. coli* and MC simultaneously.
   B) Added MC 2 hours after *E. coli* stimulation.
5. The plasma levels were measured of TNF, IL-1, IL-6, IL-8, and IL-1RA by enzyme linked immunosorbent immunoassay at time=0, 1, 2, 4, 6, and 24 hours.

C) Descriptive Results

Figure 9:
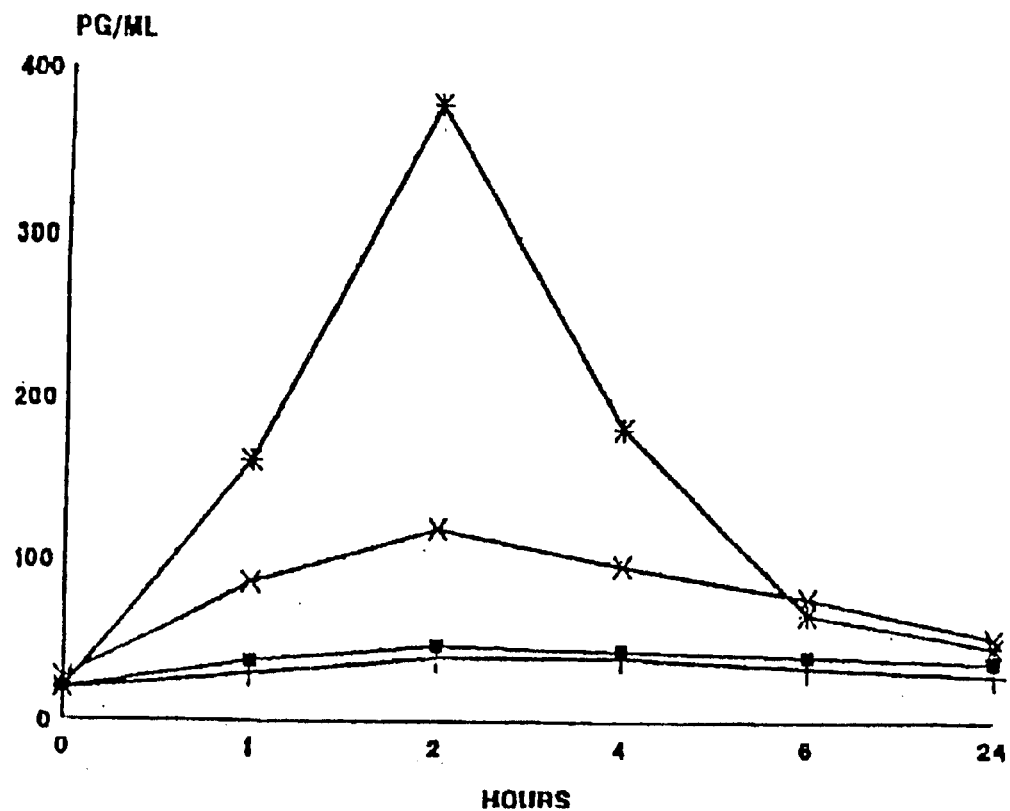

FIG. 9 shows the concentration of TNF alpha when endotoxin and microencapsulated NA are added simultaneously in vitro (only significant reductions from positive control are shown). This indicates that microencapsulated MC-TNF completely blocks the endotoxin stimulated release of TNFa. Additionally, microencapsulated IL1-NA blocks about 75% of endotoxin stimulated TNFa release.

Figure 10:
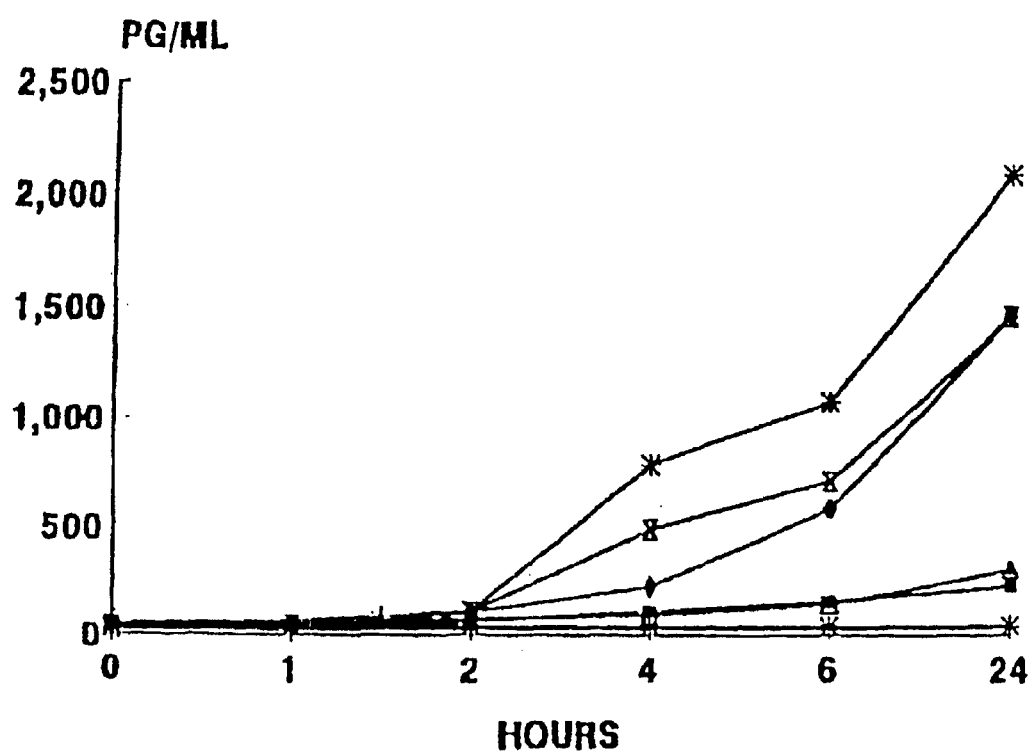

FIG. 10 shows the concentration of IL-1 beta when endotoxin and microencapsulated NA are added simultaneously in vitro (only significant reductions from positive control are shown). This indicates that microencapsulated IL1-NA completely blocks the endotoxin stimulated release of IL-1 beta. Additionally, microencapsulated TNF-NA blocks about 85% of endotoxin stimulated IL-1 beta release. IL6-NA and IL8-NA block IL-1 beta, but it is significantly less then that observed with TNF-NA, IL1RA or IL1-NA.

Figure 11:
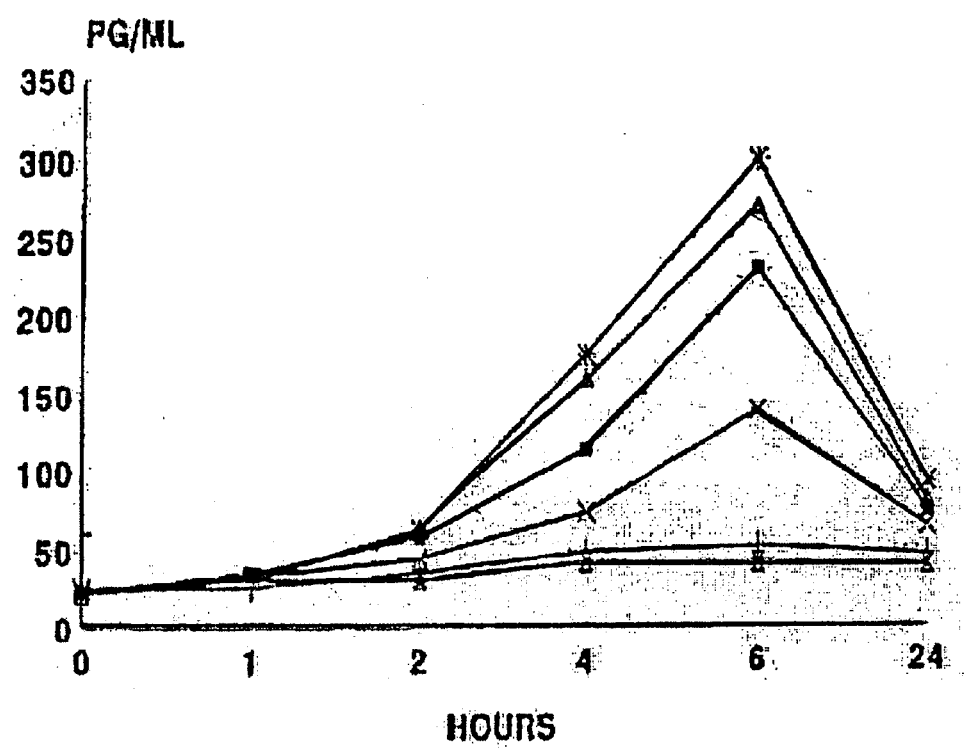

FIG. 11 shows the concentration of IL-6 when endotoxin and microencapsulated NA are added simultaneously in vitro (only significant reductions from positive control are shown). This indicates that microencapsulated IL6-NA completely blocks the endotoxin stimulated release of IL-6. Additionally, microencapsulated TNF-NA blocks about 25% of endotoxin stimulated IL-6 release. IL1-NA blocks about 50% of endotoxin stimulated IL-6 beta, while IL1RA blocks only a small but significant amount of IL-6.

Figure 12:
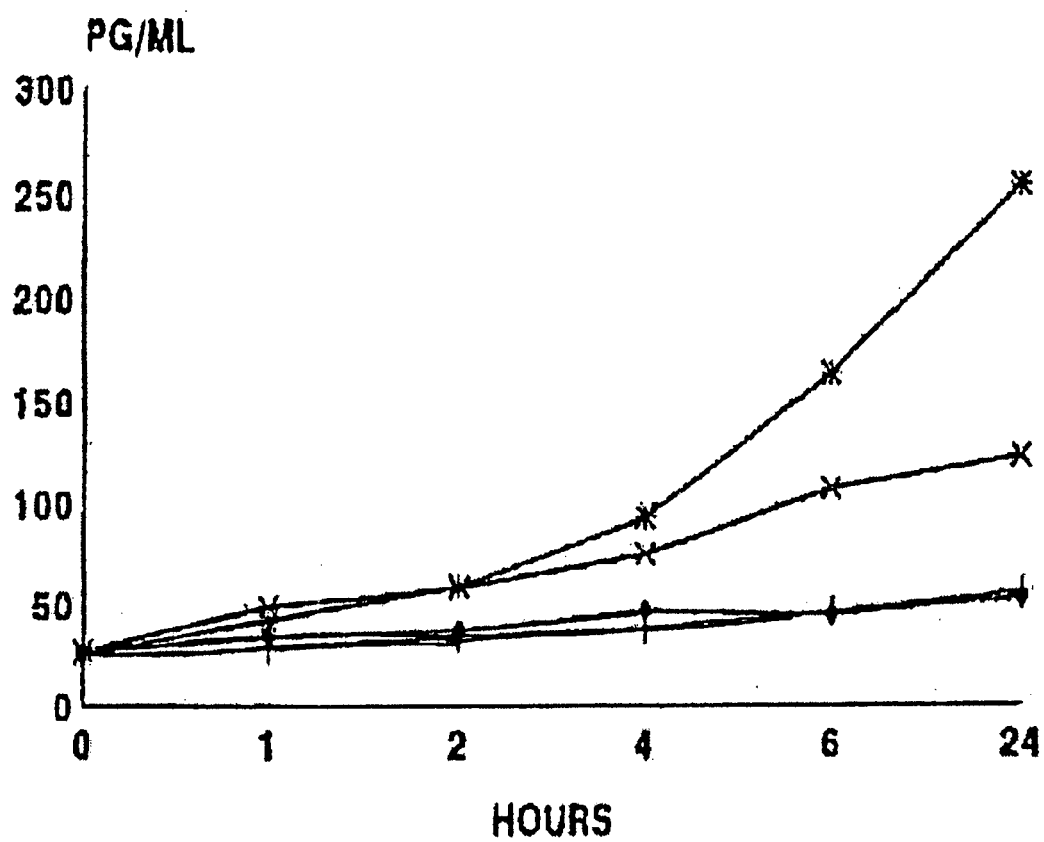
FIG. 12 shows the inhibition of IL8 following in vitro administration of anticytokine antibodies. Key: +=blank microcapsule without any neutralizing antibody or endotoxin (negative control); star=blank microcapsule and E. coli endotoxin (positive control); x=microencapsulated IL1β neutralizing antibody; diamond=microencapsulated IL8 neutralizing antibody.

FIG. 12 shows the concentration of IL-8 when endotoxin and microencapsulated NA are added simultaneously in vitro (only significant reductions from positive control are shown). This indicates that microencapsulated IL8-NA completely blocks the endotoxin stimulated release of IL-8. Additionally, microencapsulated IL1-NA blocks about 50% of endotoxin stimulated IL-8 release.

While the invention has been described in connection with certain preferred embodiments, it is not intended to limit the scope of the invention to the particular forms set forth, but, on the contrary, it is intended to cover such alternatives, modifications, and equivalents as may be included within the spirit and scope of the invention as defined by the appended claims.

2. MICROSPHERE UPTAKE BY MACROPHAGES

A) Cell Isolation Procedures

Cells were isolated from whole blood of healthy volunteers. The cells were isolated using 50 ml of glucose nutritive medium (GKN) composed of HBSS supplemented with 0.2% glucose, centrifuged at 400 g, resuspended briefly in 1 ml of distilled water in order to lyse red blood cells and restored to isotonicity using 1 ml of 1.8% w/v NaCl. The cells were then plated in 100 ml culture flasks containing 25 ml of culture medium -RPMI 1640 (Gibco Laboratories) supplemented with 10% fetal calf serum (Gibco Laboratories) for 1.5 hours. Culture medium containing non adherent cells was aspirated out, and the flask rinsed twice with GKN. The adherent cells were gently scraped off the flask using a rubber policeman, counted in a hemocytometer and tested for viability using trypan blue. The macrophages were then diluted in culture medium to obtain a final dilution of $0.5 \times 10^7$ cells in 2 ml. Two ml of cell suspension were plated in 25 ml culture flasks in a $CO_2$ incubator (37° C., 5% $CO_2$) for 1.5 hours before use.

B) Test Procedure

Figure 13:
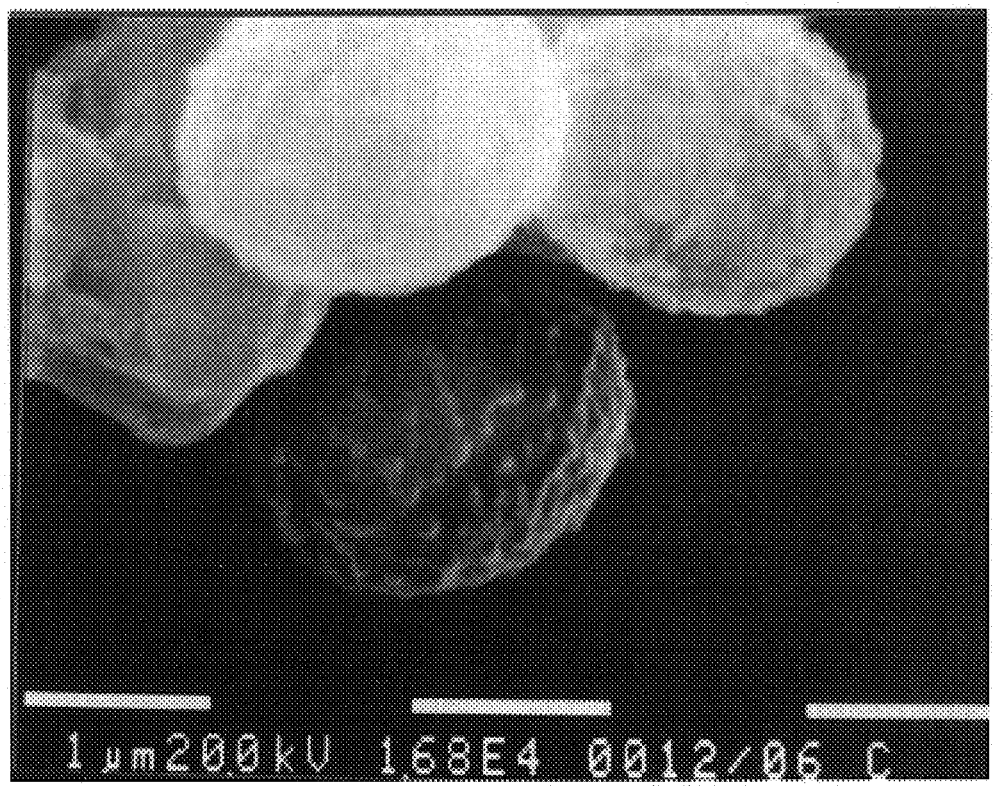
FIG. 13 is an electron micrograph of microencapsulated TNFa and IL1β neutralizing antibodies.
Figure 14:
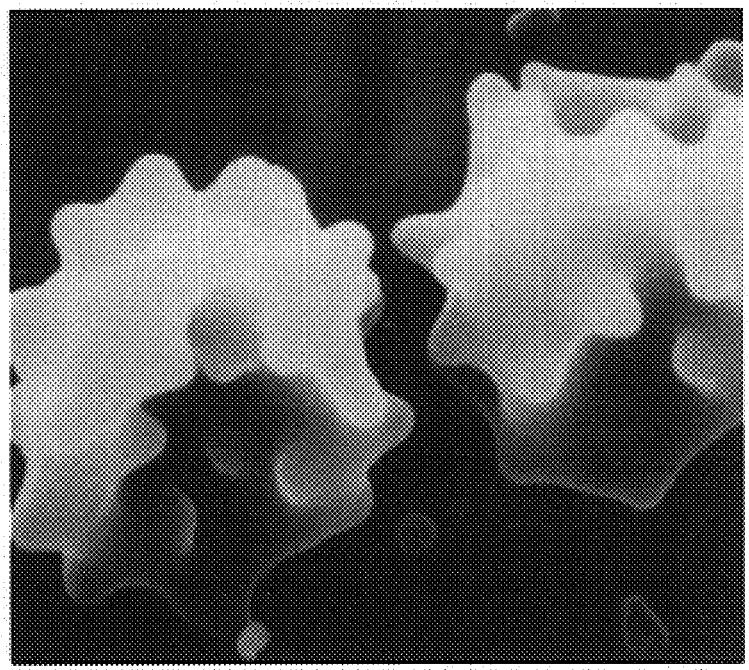
FIG. 14 is an electron micrograph of unactivated macrophages.
Figure 15:
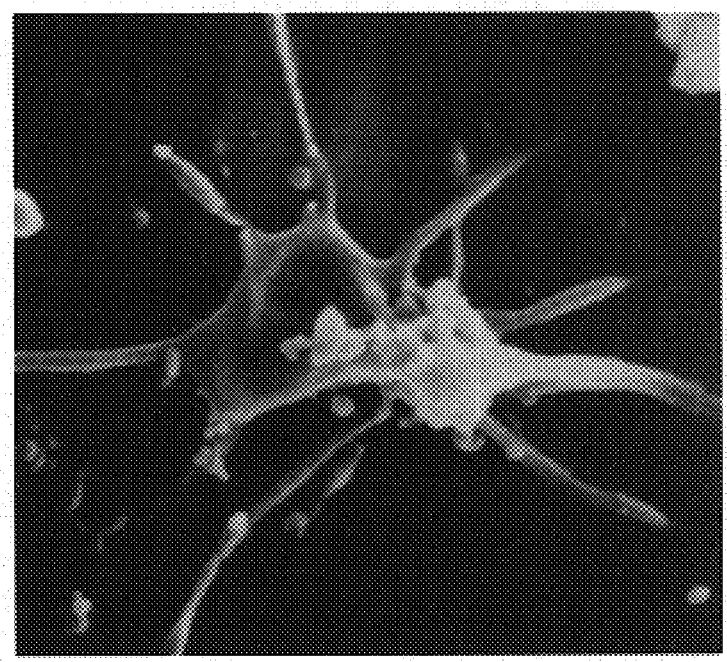
FIG. 15 is an electron micrograph of activated macrophages engulfing microencapsulated TNFa and IL1β neutralizing antibodies.
Figure 16:
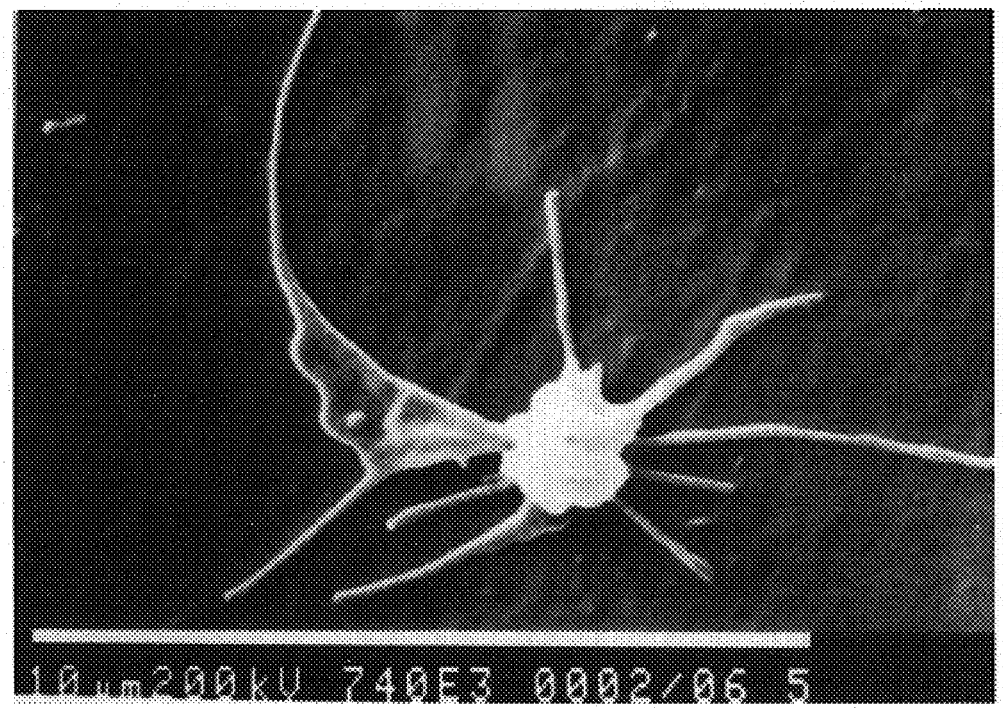
FIG. 16 is an electron micrograph of activated macrophages engulfing microencapsulated TNFa and IL1β neutralizing antibodies.

Microencapsulated TNFa and IL1β NA in combination were prepared as in example 1. 0.1 ml of microencapsulated NA in solution were added to the cell cultures. Over a 20 min period, aliquots of the cultures were scanned using an electron microscope at either 1 or 10 micron resolution. FIG. 13 shows a cluster of microcapsules that were present in the solution prior to inoculating the culture. FIG. 14 is a picture of unactivated macrophages prior to the addition of the microcapsules. FIGS. 15 and 16 are electron micrographs of activated macrophages readily phagocytosing the microcapsules.

C) Descriptive Results

These micrographs indicate that the microcapsules described in example 1 are readily phagocytosed by macrophages in vitro and would therefore be expected to undergo the same process in vivo.

3. IN-VIVO STUDIES: ENDOTOXEMIA IN RATS

A) Animals

Male Fisher rats (100–150 gm) were used in all experiments. All animals were given free access to food and water and were maintained on a 12 hr light-dark cycle.

B) Microcapsule Preparation

Microcapsules (MC) were prepared as detailed in Example 1. Microcapsules contained either TNFa-NA 1 mg/ml, IL1β-NA 2 mg/ml, or a combination of TNFa-NA and IL1β-NA in the above dose in a PBS solution. In addition, a blank microcapsule was prepared using only albumin.

C) Experimental Design

Endotoxin (ET) obtain from *Escherichia coli* 0113 obtained from commercial sources was used. Previous studies indicated that a dose of 15 mg/Kg of ET produced an $LD_{100}$ within 24 hours in untreated animals. All ET and/or microcapsules were administered in a single injection into a tail vein. Cytokine concentrations were measured as previously described.

The following groups were tested:

1—ET 15 mg/kg alone
2—ET+Blank MC
3—ET+microcapsules containing TNFa-NA
4—ET+microcapsules containing IL1β-NA
5—ET+microcapsules containing both TNFa-NA and IL1β-NA D) Results Survival data is presented in FIG. 17. No animals survived more than 36 hr in groups 1 or 2 (controls). Survival was 80% following MC TNF-NA and the combination of TNF+IL1-NA microcapsules. Survival was 100% in animals treated with MC TNF-NA alone. There was no difference in survival between any of the MC NA combinations. However, all treatments were significantly better than control ($P<0.05$, Fisher Exact Test). Inhibition of plasma TNFa and IL1β following MC NA treatment are shown in FIGS. 18 and 19. Peak TNFa was reduced >96% while peak IL1β was reduced >88% with MC NA treatment.

4. IN VIVO STUDIES: LETHAL GRAM NEGATIVE AND GRAM POSITIVE PERITONITIS IN THE RAT

A) Animals/Bacteria

Fisher rats weighing between 100–150 gm were used throughout the study. The animals were housed in a controlled environment, exposed to a 12-hour light-dark cycle, and provided free access to rat chow and water. Live bacteria were incubated in Trypticase-soy broth in a $CO_2$ hood at 37° C. and maintained at a broth concentration of $10^{10}$ cfu/mL by dilution. Gran negative bacteria were *Escherichia coli* (*E. coli*) and gram positive bacteria were *Staphylococcus aureus* (*Staph A*).

B) Microsphere Preparation

Microspheres containing neutralizing antibodies (NA) to murine TNFa and IL-1 β were prepared as described in Example 1 using human albumin as the microsphere matrix. The microsphere emulsions yielded 1.0 mg/mL of TNFa and 2.0 mg/mL of IL-1β NA. The combination used during the study was prepared by adding 0.1 mL of TNFa and 0.1 mL of IL-1β NA microspheres. The microsphere emulsion was sized by sequential reduction with high pressure liquid chromatography filters to yield a working size range of <1.0 μm for the studies.

C) Cytokine Determinations

Blood samples for plasma cytokine determinations were obtained from the rats during ether anesthesia by clipping off a small portion of tail and "milking" the tail. A direct enzymelinked immunosorbent assay ELISA analysis using murine antibodies was used to determine the plasma cytokine concentrations. Plasma TNFa and IL-1β were determined 2 hr and then every 24 hr following the bacterial challenge.

D) Experimental Design

Four protocols were used during the study. In each protocol the following groups were studied:

1–5 animals that received an intraperitoneal bacterial challenge of $1\times10^{10}$ CFU of live bacteria. (positive control)

2–5 animals that received an intraperitoneal bacterial challenge of $1\times10^{10}$ CFU of live bacteria and a 0.2 mL 100 gm intravenous injection (by tail vein) of blank microspheres daily for 3 days.

3–10 animals that received an intraperitoneal bacterial challenge of $1\times10^{10}$ CFU of live bacteria and twice daily injections of either intraperitoneal gentamicin 15 mg/kg/day (gram negative protocol) or vancomycin 30 mg/kg/day (gram positive protocol) for 5 days.

4–10 animals that received an intraperitoneal bacterial challenge of $1\times10^{10}$ CFU of live bacteria and a 0.2 mL/100 gm intravenous injection (by tail vein) of TNFa and IL-1β NA microspheres (daily for 3 days) and either intraperitoneal gentamicin 15 mg/kg/day (gram negative protocol) or vancomycin 30 mg/kg/day (gram positive protocol) for 5 days.

5–10 animals that received an intraperitoneal bacterial challenge of $1\times10^{10}$ CFU of live bacteria and an intravenous injection (by tail vein) of TNFa (100 μg/100 gm) and IL-1β (200 μg/100 gm) NA unencapsulated (daily for 3 days) and either intraperitoneal gentamicin 15 mg/kg/day (gram negative protocol) or vancomycin 30 mg/kg/day (gram positive protocol) for 5 days.

6–10 animals that received an intraperitoneal bacterial challenge of $1\times10^{10}$ CFU of live bacteria and a 0.2 mL/100 gm intravenous injection (by tail vein) of TNFa and IL-1β NA microspheres (daily for 3 days) without antibiotics.

7–10 animals that received an intraperitoneal bacterial challenge of $1\times10^{10}$ CFU of live bacteria and an intravenous injection (by tail vein) of TNFa (100 μg/100 gm) and IL-1β (200 μg/100 gm) NA unencapsulated (daily for 3 days) without antibiotics.

The dosing of NA microspheres, unencapsulated NA, and blank microspheres was performed every 24 hours for 3 days or until death. The following 4 protocols were used during the study:

1—Simultaneous addition of bacterial challenge and intravenous treatment regimen using *E. coli*.
2—Simultaneous addition of bacterial challenge and intravenous treatment regimen using *Staph A*.
3—Addition of bacterial challenge 4 hours prior to intravenous treatment regimen using *E. coli*.
4—Addition of bacterial challenge 4 hours prior to intravenous treatment regimen using *Staph A*.

Survival in all four protocols was determined over 5 days.

E) Results

Simultaneous Treatment:

FIGS. 20 and 21 depict the survival of animals in which neutralizing antibodies were administered simultaneously with the bacterial challenge with either *E. coli* or *Staph A*. In animals that received bacteria alone, survival was 0% by 48 hours. By 72 hours, survival was greater in animals treated with microencapsulated neutralizing antibodies, both with and without antibiotics, versus other treatment groups (p<0.0004). After the cessation of antibiotics and MC NA on day 3, survival remained 100% in the animals that had received antibiotics in conjunction with MC NA (p<0.0001 vs. positive control), but fell in animals that only received MC NA (p<0.005 vs MC NA+antibiotics). In addition, no significant difference was observed in survival between animals treated with unencapsulated NA antibiotics alone, or unencapsulated NA and antibiotics compared to no treatment.

Delayed Treatment:

FIGS. 22 and 23 depict the survival of animals in which neutralizing antibodies were administered 4 hours after a bacterial challenge. Animals that received bacteria alone (positive control) were all dead by 48 hours. Survival was 100% in animals treated with MCNA with antibiotics versus 50% in animals treated with MCNA without antibiotics (NS), by 72 hours. After the cessation of antibiotics and MCNA on day 3, survival remained 100% in the animals that had received antibiotics in conjunction with MCNA (p<0.0001 vs. positive control), but fell to <20% in animals that only received MCNA (p<0.0001 vs MCNA+antibiotics). No significant difference was observed in survival between animals treated with unencapsulated NA, antibiotics alone, or unencapsulated NA and antibiotics, compared to no treatment.

Cytokine Concentrations

TNFa concentration during simultaneous and delayed treatment are depicted in FIGS. 24, 25, 26 and 27. MCNA were only capable of suppressing peak TNFa release if given simultaneously with bacterial challenge. FIGS. 28, 29, 30 and 31 shown the IL1β concentrations following MCNA therapy. Antibiotic therapy in combination with MCNA afforded significant reduction in peal IL1β.

These data indicate that MCNA afford complete protection from a lethal peritonitis bacteremia in rats from both gram positive and negative bacteria when given in combination with antibiotics. The effect is also observed even 4 hours after the bacterial challenge and occurs independent of the peak release of TNFa.

Example 4

1. INHIBITION OF OKT3 INDUCED CYTOKINE RELEASE

A) Introduction

Cytokines are felt to be one of the major contributing factors in the rejection of transplanted organs. Induction of cytokines has been observed in a variety of diseases including rheumatoid arthritis, lupus, ANCA positive glomerulonephritis, and organ rejection. The release of cytokines in areas of local or systemic immune reaction is responsible for a wide variety of host responses including up-regulation of the immune system, chemotactic factors, and local inflammatory response which may cause the eventual loss of a transplanted organ. TNFa release has been implicated in liver transplant rejection, experimental lung allograft rejection in the rat, experimental cardiac or renal transplantation. Recent studies have demonstrated in situ production of the cytokines TNFa and IL1β in liver and kidney transplants and in ANCA positive glomerulonephritis. These studies suggest that local release of cytokines by macrophages, which produce cytokines in large concentrations, may play a pivotal role in organ rejection or the inflammatory processes of glomerulonephritis.

OKT3 is a murine monoclonal antibody to the CD3 antigen of human T cells and is used to treat transplant rejection. The high incidence of adverse reactions associated with OKT3 is thought to be related to the induction of cytokines. The purpose of this study was to determine if microencapsulated (MC) neutralizing antibodies (NA) to human TNFa and IL1β which are readily phagocytized by macrophages can inhibit the release of TNFa, IL1β, and IL6 following OKT3 challenge in vitro.

B) Methods

Microcapsules were prepared using the method from Example 1 using an albumin matrix. Blood was collected from 10 healthy subjects and separated into aliquots for the following groups.

Grp 1) Blank MC
Grp 2) OKT3 1 µg/mL+Blank MC
Grp 3) TNFa NA 1 µg/mL+IL1β NA 2 µg/mL+OKT3 1 µg/mL. Aliquots were incubated at 37° C. for 24 hr. Blood was assayed for TNFa, IL1µ, and IL6 at 0, 2, 6, 24 hr by ELISA.

C) Results

OKT3, in normal therapeutic concentrations, stimulated TNFa, IL1β, and IL6 release and produced elevations in these cytokines comparable to that observed with an endotoxin (100 ng/mL) challenge. Peak TNFa was 655±71 pg/mL in Grp 2 vs 72.5±9.7 pg/mL in Grp 3 (p<0.0001) FIG. 32. IL1β in Grp 2 was reduced 94% at 24 hr with MC NA FIG. 33. Peak IL6 was decreased from 664±60 to 83±7.7 pg/mL following MC NA treatment FIG. 34. No increase in any cytokine was observed in Grp 1.

Example 5

USE OF A COMBINATION OF MICROENCAPSULATED M-CSF-ALBUMIN AND MICROENCAPSULATED METHOTREXATE-PLGA IN CANCER THERAPY

A) Introduction

Macrophage colony stimulating factor (M-CSF) is a biological response modifier, primarily produced by monocytes which stimulates the formation of macrophage colonies. Major activities of M-CSF includes: the enhancement of antibody-dependent cell-mediated cytotoxicity by monocytes and macrophages, stimulation of microglial cell proliferation, and formation of macrophage colonies in bone marrow. M-CSF was utilized in the microencapsulated form to enhance the immune system during chemotherapy with methotrexate.

B) Synthesis and Preparation of Microspheres

This portion of the patent deals with the formulation and the preparation of the microspheres. Both methotrexate (MTX) and M-CSF were microencapsulated within poly lactic co-glycolic acid (PLGA) and albumin, respectively. The release rate of the microencapsulated agents and the stability studies were carried out. These microencapsulated agents were used in-vivo in melanoma cancer therapy.

1) Synthesis Of PLGA-MTX Conjugate

Altering the physical and/or chemical properties of a cancer agent itself through chemical modification or by attachment to a carrier system could be a formidable tool for increasing the effectiveness of the drug. However, the carrier should meet reasonable criteria of pharmaceutical formulation such as homogeneity, purity and stability. The carrier should have adequate functional groups for chemical fixation to attain high drug-carrying capacity. Moreover, the carrier and the metabolic products should undergo biodegradation at a reasonable rate or at least should not show any serious accumulation in the body.

Amides are of great importance in biochemistry. The linkages that join individual amino acids together to form proteins are primarily amide linkage. As a consequence, much research has been carried out to find newer and milder procedures for amide synthesis. One useful reagent is the compound dicyclo-hexylcarbodimiide (DCC). DCC catalyzes the formation of amide bonds between carboxylic acids and amines by activating the carboxylate to form an O-acylurea. This intermediate either can be attacked by the amine to form the amide or it can be attacked by a second carboxylate to give the anhydride which can then be attacked by the amine, giving the amide and regenerating one of the carboxylates. In the synthesis of PLGA-MTX conjugate, DCC promotes amide formation by reacting with the carboxyl group on PLGA and activating it towards the amino group on MTX.

Reaction of PLGA 50:50 (2% w/v) with 1,3-dicyclohexyl-carbodiimide (DCC) (16% w/v) and MTX (1% w/v)) was carried out at room temperature in 800 Ul volume of 1-methyl-2-pyrrolidinone. The reaction was carried out using 5 different ratios of carbodiimide to PLGA (1:1, 2:1, 4:1, 8:1 and 12:1). The reaction mixture was stirred in dark for 4 h in a shaker and stored at room temperature for 24 h. The conjugate was washed 3 times with distilled water and centrifuged at 1600 rpm. The precipitate was dried in a vacuum over night.

Synthesis of radioactive PLGA-MTX conjugate was carried out in similar manner, however, MTX was replaced with radiolabeled (C-14) MTX (0.5 Uci). The identity of the conjugate was confirmed using infrared (IR) spectroscopy (Perkin-Elmer, Norwalk, Conn.), NMR, HPLC with ultra-violet (UV) detection (Beckman, Fullerton, Calif.) and thin layer chromatography. IR spectra of PLGA, MTX, DCC and the MTX-PLGA conjugate were recorded using sodium iodide disks. The extent of conjugation was confirmed by determining the percent of free radioactive MTX (H-3) which did not conjugate to PLGA via the use of a liquid scintillation counter (LSC). The extent of conjugation was also determined by analyzing free MTX content using high-performance liquid chromatography (HPLC) with UV detection at 305 nm.

FIG. 35 illustrates the extent of conjugation as a function of different ratios of DCC to PLGA. Maximal conjugation (55%) was observed at a DCC to PLGA ratio of 8:1, where as a 1:1 ratio of DCC to PLGA produced a meager 6% conjugation. However, on increasing the ratio of DCC:PLGA to 12:1 no further increase (54.3%) in the extent of conjugation was observed.

2) Formulation of PLGA-MTX microspheres

PLGA-MTX conjugate was dissolved in 10 ml of methylene chloride. The solution was dispersed into distilled water containing 2% w/v polyvinyl alcohol and 5% v/v Tween 80 using a homogenizer. The emulsion was then placed into an ice bath and was sonicated using a Branson Sonifier probe for 10 minutes to achieve microspheres less then a 1 micron in size. The size of microspheres were monitored with an electron microscope and a light microscope. The emulsion stirred with a magnetic stirrer for 24 h to allow methylene chloride to evaporate, thereby hardening the microspheres. The PLGA-MTX microspheres were centrifuged out at 6000 rpm for 25 minutes and washed 3 times with distilled water. The microspheres were then purified by dialysis using PBS (1000 ml changed every 12 hour) for 48 hr, followed by deionized water for 12 hr. The purified microspheres were allowed to dry in a desiccator and stored at −30° C.

3) Synthesis of radio-labeled microspheres

Synthesis of radioactive PLGA-MTX conjugate was carried out in similar fashion, however, MTX was replaced with radiolabeled (C-14) MTX (0.5 Uci). The identity of the conjugate was confirmed using infrared (IR) spectroscopy, ultraviolet (UV), NMR and thin layer chromatography. IR spectra of PLGA, MTX, DCC and the conjugate were recorded using sodium iodide disks. The conjugate were analyzed for drug content using U.V. absorbance at 305 nm.

4) Sizing of the conjugate microspheres MTX-PLGA conjugate microspheres were filtered sequentially through 8 μm and 1 μm filters to obtain microspheres less then 1 μm in diameter which were used in the studies.

C) Stability of MTX-PLGA Conjugate in Phosphate Buffer

The stability of the conjugate was determined using dialysis technique. The system consisted of a dialysis bag (12,000–14,000 M.W.) containing radiolabeled MTX-PLGA microsphere conjugate (n=4) equivalent to 2 mg of MTX (C-14) which was stirred at=100 rpm. The dialysis medium consisted of phosphate buffer (Ph 7.4). The external buffer reservoir was sampled periodically for 3 days. The radioactivity of the samples reflective of free MTX, was measured using liquid scintillation counter (LSC).

IN-VITRO DEGRADATION OF MTX-PLGA CONJUGATE IN PLASMA AND RAT LIVER HOMOGENATE:

In an attempt to determine the degradation of MTX from the microspheres, an in-vitro degradation study in plasma and liver homogenate were carried out. The dialysis bag consisted of radiolabeled MTX-PLGA conjugate (n=4) equivalent to 2 mg of MTX (C-14) as described earlier. Either rat liver homogenate equivalent to 2 g of liver in 5 cc of phosphate buffer saline (Ph 7.4) or plasma (5 Ml) were added to the dialysis bag. The external buffer reservoir consisting of phosphate buffer saline (Ph 7.4) was sampled at predetermined intervals and the radioactivity was analyzed by LSC.

FIGS. 36 and 37 illustrates the percentages of MTX remaining in the MTX-PLGA conjugate after incubation with various mediums. The three mediums which were studied were rat liver homogenate, rat plasma and phosphate buffer (Ph 7.4). The MTX-PLGA microspheres were stable in the presence of phosphate buffer (Ph 7.4) for a period of 3 days with maximum release of MTX at 3.5% at the end of the 72 hour study. The release of MTX from the conjugated microsphere is probably due to hydrolysis of the MTX-PLGA complex. In presence of either liver homogenate or plasma, the microspheres demonstrated a bi-exponential release profile. There was an initial 8 hour rapid release period, and thereafter the release rate was slower. In the case of liver homogenate, after 48 hours of incubation only 25% of MTX was released from the conjugate. The initial and the secondary half life of release of MTX from the conjugate in presence of liver homogenate as 0.212 and 1.68 hours respectively. Plasma displayed only 17.25% MTX release over 72 hours. The initial and the secondary half life release of MTX from the conjugate in presence of the plasma was 1.11 and 3.5 hours respectively. The release patterns of phosphate buffer, plasma and liver homogenate were significantly different ($p<0.05$).

This release pattern observed from both the liver homogenate and plasma suggests that the initial rapid release over 8 hour period appears to be due to break up of MTX-PLGA bonds on the surface of the microspheres primarily due to protease enzymes found in the liver homogenate and plasma. However, it takes longer time period for the enzymes to hydrolyze the amide bonds in the interior of the microspheres as reflected by the slow secondary release profile.

Overall, the conjugated microspheres were stable with only 2% release of MTX in the presence of phosphate buffer at Ph 7.4 indicating a stable microsphere formulation. In conclusion, the coupling of MTX to PLGA using an intermediate coupling agent such as DCC was optimal (55%) at ratio of 8 to 1 (DCC to PLGA) and successful in releasing of the intact MTX from the PLGA complex. This suggests that MTX-PLGA conjugate is a good candidate for drug targeting experiments to the tumor sites in-vivo.

RETENTION OF MTX ACTIVITY IN THE MTX-PLGA CONJUGATE

MTX reactivity in the PLGA conjugate was assessed by obtaining the supernatant of the above study "in-vitro degradation of MTX-PLGA conjugate in liver homogenate". The activity of MTX released from the microspheres was measured by HPLC and ELISA and the results were compared to that of unconjugated MTX. The free MTX from the degradation study was analyzed by HPLC in order to determine its concentration level. Once the concentration of free MTX was determined we compared the biological activity of free MTX to that of the unconjugated MTX by ELISA. The results from this experiment could determine the biological activity of the conjugated MTX and whether conjugation of MTX to PLGA alters the structural and biological activity of the conjugated MTX.

MTX activity in PLGA conjugate was assessed relative to that of unconjugated MTX. By comparing the results from the ELISA studies, both the conjugated MTX (100 ng/ml) and unconjugated MTX (100 ng/ml) had similar binding affinity to the monoclonal antibody. Furthermore, to determine if MTX had lost or gained extra functional groups during synthesis or degradation period, HPLC analysis of MTX was carried out. Both the conjugated and unconjugated MTX (100 ng/cc) had similar retention time. Therefore, from both the ELISA and HPLC study, it is possible to predict that there was no loss of activity of MTX when conjugation synthesis was carried out.

FORMULATION OF ALBUMIN MICROSPHERES CONTAINING M-CSF

Macrophage colony stimulating factor (M-CSF) is an immunomodulatory agent which activates macrophages and induces antitumor immunity in-vitro. Unfortunately, several obstacles, such as its rapid catabolism and short half life remain to be overcome for successful use of M-CSF. Hence, it is prudent to develop a sustained release formulation targeted to macrophages, and as a result, decrease the rapid catabolism, increase the half life and obtain a target delivery system. Albumin microspheres increase opsonization and accelerate macrophage phagocytosis. Phagocytosed albumin microspheres than can gradually undergo degradation in the macrophages, followed by release of M-CSF from the albumin microspheres in the cells.

Albumin microspheres containing M-CSF were prepared by polymerization from a water-in-oil emulsion. A 12.5% solution of albumin in 0.07 M phosphate buffer (Ph 7.6) was added to 0.8 mg/ml of M-CSF. The solution was added to 25 Ml olive oil and stirred at 2000 rev $min^{-1}$ for 15 minutes. Glutaraldehyde solution (650 µL, 25% v/v) was added to cross-link the albumin and the emulsion stirred for an additional 15 minutes. The microspheres were collected by centrifugation at 10,000 rpm for 20 min and washed with light petroleum followed by ethanol. The size of albumin microspheres were determined under light microscope (size=3–5 µm).

ASSESSMENT OF DRUG INCORPORATION

The amount of M-CSF entrapped in microspheres was estimated by preparing radioactive M-CSF (I-125) albumin microspheres. The final product was dried and the amount of incorporated M-CSF was determined using gamma well counter.

IN-VITRO RELEASE OF M-CSF FROM ALBUMIN MICROSPHERES

Albumin microspheres, 20 mg, containing 200 µg M-CSF were suspended in 50 Ml 0.07 M phosphate buffer saline (Ph 7.4) in a beaker at 37° C. Using a magnetic stirrer, the suspension was stirred continuously at a constant speed. Aliquots of 0.5 Ml were removed at various times up to 5 days. The samples were centrifuged at 3000 rev $min^{-1}$ for 10 minutes and the amount of drug released from the microspheres determined by analyzing 0.1 mL supernatant by ELISA technique. All aliquots removed from the suspensions were replaced with 0.5 mL of phosphate buffer (pH 7.4).

The in-vitro drug release profile of M-CSF from albumin microspheres is shown in FIG. 38. In presence of PBS, the microspheres demonstrated a tri-exponential release profile. There was an initial 10 hour rapid release period ($k=0.111$ $hr^{-1}$, half-life=6.24 hr), and thereafter the release rate was slower ($k=0.021$ $hr^{-1}$, half-life=33 hr; $k=0.0046$ $hr^{-1}$, half-life=149 hr). Albumin microspheres released 50% of the M-CSF with in the first 5 days of the study.

The albumin microspheres released methotrexate in-vitro in a biphasic manner with a initial rapid release over 6 hour. The initial rapid release appeared to be due to physically adsorbed MTX on the surface of the albumin microspheres. The slower secondary release of MTX was due to erosion of the microsphere over time. The encapsulation of M-CSF inside the albumin microspheres enables albumin microspheres to retain the activity of M-CSF for a prolonged time. The degradation studies suggests that degradation occurred by simple surface erosion.

IN-VIVO STUDIES OF A COMBINATION THERAPY OF MICROENCAPSULATED M-CSF AND MICROENCAPSULATED METHOTREXATE IN MELANOMA TUMORS

In vivo studies were carried out to assess the effect of the above combination therapy, both in the solution form and in the microencapsulated form in the treatment of cancer, in order to examine any possible advantages of the microencapsulated form of the drugs. The cytokine levels (eg. TNFa and IL1β were also evaluated after treatment.

A) Induction of Tumors in Mice

Male C57BL/6 mice weighing approximately 18–20 g were anesthetized with light ether vapor and were injected subcutaneously with B-16 cells ($1 \times 10^6$ cells). Their weights, tumor size and survival rate (in days) were measured daily. The tumor size was followed by measuring the long axis of the tumor daily. The study began once the tumor size reached 0.5 cm in diameter. The animals were divided into control and treatment groups. The control groups received phosphate buffered saline, blank PLGA microspheres or blank albumin microspheres. The treated groups received the following dosing schedule: Methotrexate solution (2 mg/kg or 15 mg/kg) administered s.c. daily or every three days. The M-CSF solution (10 microgram/kg or 100 microgram/kg) administered i.p. daily. The MTX microspheres (2 mg/kg or 15 mg/kg) and/or the M-CSF microspheres (10 microgram/kg or 100 microgram/kg) administered s.c. and i.p. respectively, alone or in combination therapy.

A significant difference ($p<0.05$) was observed in the groups which received s.c. injections of 2 mg/kg or 15 mg/kg of the MTX microspheres versus the MTX solution administered every three days FIG. 39. The mean survival for the 2 mg/kg of the MTX microspheres administered ever 3 days was 18.4 versus 12.8 for the 2 mg/kg of the MTX solution treated groups. The mean survival time for the 15 mg/kg of the MTX microspheres administered every 3 days was 20.2 versus 14.2 for the 15 mg/kg of the MTX solution treated groups. FIG. 40 represents the dose response of the M-CSF solution versus the M-CSF microspheres at the dosed of 10 or 100 microgram/kg doses in malignant melanoma mice. A significant difference was observed in the survival time between the M-CSF microsphere and the solution treated groups at 10 microgram/kg dose. The mean survival time in the M-CSF microsphere (10 microgram/kg) treated group was 20.8 versus 14,2 days for the M-CSF solution treated groups. FIG. 41 illustrates the effect of the microencapsulation versus the free solution of M=CSF with MTX in the combination therapy of malignant melanoma. The combination therapy of the microencapsulated M-CSF (10 microencapsulation/kg) with the MTX microspheres (15 mg/kg) showed a significant increase in the survival rate than the free solutions of M-CSF with MTX at the same doses.

B) Determination of TNFa and IL-1β Levels in Mice with Malignant Melanomas

Cytokines are important mediators and modulators of many physiological systems, especially in immunological processes. Imbalances in the production of cytokines can have profound effects and may ultimately contribute to pathogenesis of diseases. For example, imbalances in the levels of TNF can ultimately lead to such diseases as malignancy, rheumatoid arthritis, capillary leak syndrome, pulmonary fibrosis, septic shock and parasitosis.

Interleukin-1, also called lymphocytes activating factor, is produced by a number of cell types, including monocyte and macrophage cell lines, natural killer cells (NK) and B cell lines. Some IL-1 activities include: activation of T cells, induction of IL-2 receptors, induction of fever and co-stimulation of thymocyte proliferation. Also, IL-1a is an indicator for macrophage activation. During macrophage activation, they secrete high concentration of IL-1a into the circulation.

FIGS. 42 and 43 lists the concentration of IL-1β in mice with malignant melanomas. FIGS. 44 and 45 shows the concentration of TNFa in mice with melanoma there was a significant increase ($p<0.05$) in the TNFa levels (204 pg/cc) when the animals were treated with the combination of MTX microspheres (15 mg/kg) and the M-CSF microspheres (100 microgram/kg) than the control (31.5 pg/cc). The TNFa levels were significantly higher in the microspheres combination treated group than the solution combination treated group. TNFa is a good indicator of macrophage activation. The increased survival rate may have occurred because M-CSF activated the immune system and allowed the activated macrophages to slow the growth of the tumors.

C) Conclusions

The combination therapy of the microencapsulated M-CSF and MTX were more effective in increasing the survival rate than the free solutions. From the in-vitro stability data as well, it is evident that the microencapsulated agents are protected from degradation resulting in an increased half-life and a sustained release profile. The microencapsulation technique enabled the drug release from the microcapsule in a sustained release fashion, thus the tumor cells were exposed to these agents for a longer time period and hence survival rate was increased significantly.

SUMMARY

The above methodology of preparation may also be used to microencapsulate cytokines, lymphokines and other biological response modifiers or drugs for use in the microencapsulated form, in cancer treatment, since some of these agents may not be very effective in the non-microencapsulated form as has been seen in all the preceding Examples 1–5.

We claim:

1. A method of administering a substance to a subject having an immune modulated disease, comprising the steps of:
   (a) preparing a microencapsulated composition, comprising the steps of
      i) providing an aqueous phase of a solubilized amount of an antibody or protein material to be encapsulated, said material being solubilized in phosphate buffered saline;
      ii) mixing said solubilized material with an amount of biodegradable and nonantigenic albumin dissolved in water or phosphate buffered saline to form an aqueous phase mixture;
      iii) adding said aqueous phase mixture of step ii) to an amount of olive oil;
      iv) emulsifying said aqueous phase mixture formed in step iii) to form microspheres of encapsulated material; and,
      v) contacting said encapsulated microspheres with a crosslinking agent for a time sufficient to crosslink at least a portion of said microspheres,
   such that said crosslinked microspheres have bioactivity and such that denaturization is substantially prevented; and,
   b) administering to said subject a therapeutically effective amount of said crosslinked microspheres.

2. The method of claim 1, further comprising after step (a)(ii) and before step (a) (iii), the step (a)(vi) cooling said mixture of step (a)(ii).

3. The method of claim 2, further comprising step (a)(vii) cooling and maintaining said oil of step (a)(iii) at a cooled temperature prior to the addition of said aqueous phase mixture of step (a)(ii).

4. The method of claim 3, wherein said cooling of said olive oil is 5° C.

5. The method of claim 3, further comprising after step (a)(v) the step (a)(viii) washing said microspheres.

6. The method of claim 5, further comprising after step (a)(viii) the step (a)(ix) sizing said washed microspheres.

7. The method of claim 1, wherein said material is selected from the group consisting of polyclonal antibodies, monoclonal antibodies, and mixtures thereof.

8. The method of claim 1, wherein said material comprises an antibody to a material selected from the group consisting of TNF-alpha and interleukin-1 receptor antagonist.

9. The method of claim 1, wherein said material comprises a neutralizing antibody to a cytokine.

10. The method of claim 9, wherein said neutralizing antibody is selected from the group consisting of antibodies to TNF-alpha, IL-1β, IL-6, IL-8, and IL-1RA.

11. The method of claim 1, wherein said microspheres have an average diameter of from about 0.22 micron to about 10 microns.

12. The method of claim 1, wherein said microspheres have an average diameter of from about 0.22 micron to about 0.8 microns.

13. The method of claim 1, wherein said mixture is emulsified by sonification.

14. The method of claim 1, wherein said crosslinking agent is glutaraldehyde.

15. A method of administering a substance to a subject having an immune modulated disease, comprising the steps of:

a) preparing a microencapsulated composition, comprising the steps of:
  i) providing a material comprising an anticytokine neutralizing antibody or mixture of anticytikine neutralizing antibodies that has been solubilized in phosphate buffered saline (PBS) to form an aqueous mixture;
  ii) mixing said solubilized material with an amount of biodegradable and nonantigenic albumin dissolved in water or PBS to form an aqueous mixture;
  iii) adding said aqueous phase mixture of step ii) to an amount of olive oil in a hydrophobic phase;
  iv) emulsifying said aqueous phase mixture formed in step iii) by sonification to form microspheres of encapsulated material; and,
  v) contacting said encapsulated microspheres with an amount of glutaraldehyde for a time sufficient to crosslink at least a portion of said microspheres;
  vi) washing said microspheres;
  vii) sizing said microspheres such that said crosslinked microspheres have bioactivity and such that denaturization is substantially prevented; and b) administering said crosslinked microspheres to a subject such that said encapsulated microspheres are engulfed by a target organ, resulting in the intracellular release of said material.

* * * * *